(12) United States Patent
Kajino et al.

(10) Patent No.: US 7,816,552 B2
(45) Date of Patent: Oct. 19, 2010

(54) INTERMEDIATE OF 6-SUBSTITUTED 1-METHYL-1-H-BENZIMIDAZOLE DERIVATIVE AND METHOD FOR PRODUCING SAME

(75) Inventors: Hisaki Kajino, Kanagawa (JP); Hiroshi Miyamoto, Kanagawa (JP); Rei Okazaki, Kanagawa (JP); Yutaka Ikeuchi, Kanagawa (JP)

(73) Assignee: Sankyo Company, Limited, Tokyo (JP)

( * ) Notice: Subject to any disclaimer, the term of this patent is extended or adjusted under 35 U.S.C. 154(b) by 316 days.

(21) Appl. No.: 11/664,140

(22) PCT Filed: Sep. 26, 2005

(86) PCT No.: PCT/JP2005/017573

§ 371 (c)(1),
(2), (4) Date: Jan. 7, 2008

(87) PCT Pub. No.: WO2006/035685

PCT Pub. Date: Apr. 6, 2006

(65) Prior Publication Data

US 2009/0023929 A1    Jan. 22, 2009

(30) Foreign Application Priority Data

Sep. 28, 2004    (JP) .............................. 2004-282064

(51) Int. Cl.
C07C 271/28    (2006.01)
C07C 217/90    (2006.01)
(52) U.S. Cl. ........................................ 560/21; 564/280
(58) Field of Classification Search .................. 560/21; 564/280
See application file for complete search history.

(56) References Cited

U.S. PATENT DOCUMENTS

| 4,863,482 A | 9/1989 | Junino et al. |
| 2004/0082583 A1 | 4/2004 | Cheung et al. |

FOREIGN PATENT DOCUMENTS

| EP | 0 385 850 A2 | 9/1990 |
| EP | 1 022 272 A1 | 7/2000 |
| EP | 1 191 019 A1 | 3/2002 |
| JP | 9-295970 A | 11/1997 |
| JP | 11-193276 A | 7/1999 |
| JP | 2003-238406 A | 8/2003 |
| WO | WO 02/44156 A2 | 6/2002 |
| WO | WO 2003/053440 A1 | 7/2003 |

OTHER PUBLICATIONS

Junya Ohmori et al., "Novel AMPA Receptor Antagonists: Synthesis and Structure-Activity Relationships of 1-Hydroxy-7-(1H-imidazol-1-yl)-6-nitro-2,3(1H,4H)—quinoxalinedione and Related Compounds," *J. Med. Chem.*, vol. 39, pp. 3971-3979, (1996), USA.
English-language International Preliminary Report on Patentability and Written Opinion of the International Searching Aughority, dated Apr. 12, 2007 for International application PCT/JP2005/017573 filed Sep. 28, 2005; Applicants: Sankyo Company Limited et al.
Junya Ohmori et al., "Novel AMPA Receptor Antagonists: Synthesis and Structure-Activity Relationships of 1-Hydroxy-7-(1H-imidazol-1-yl)-6-nitro-2,3) (1H, 4 H)—quinoxalinedione and Related Compounds", *Journal of Medicinal Chemistry*, (1996), 39, 3971-3979.
Supplementary European Search Report dated Oct. 24, 2008 in European Application EP 05785694.

*Primary Examiner*—Kamal A Saeed
*Assistant Examiner*—Kristin Bianchi
(74) *Attorney, Agent, or Firm*—Frishauf, Holtz, Goodman & Chick, P.C.

(57) ABSTRACT

A method for preparing a compound having the following formula (I)

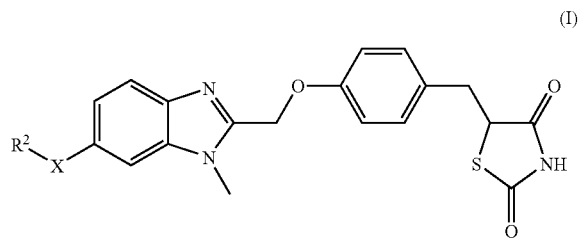

by reducing a nitro group of the following formula (III)

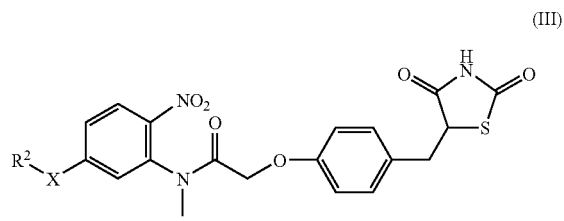

followed by carrying out an intramolecular dehydration condensation, wherein $R^2$ is hydrogen, alkyl, cycloalkyl, phenyl or a 5- or 6-membered heterocyclic, and X is oxygen, sulfur or nitrogen.

12 Claims, No Drawings

INTERMEDIATE OF 6-SUBSTITUTED 1-METHYL-1-H-BENZIMIDAZOLE DERIVATIVE AND METHOD FOR PRODUCING SAME

CROSS-REFERENCE TO RELATED APPLICATION

This application is a United States national phase application of International application PCT/JP2005/017573 filed Sep. 26, 2005.

TECHNICAL FIELD

The present invention relates to a procedure for the preparation of a 6-substituted-1-methyl-1-H-benzimidazole derivative and a synthetic intermediate thereof.

BACKGROUND ART

6-Substituted-1-methyl-1-H-benzimidazole derivatives are known to exert excellent insulin resistance improving activity, blood glucose lowering activity, anti-inflammatory action, immunomodulating activity, aldose reductase inhibitory activity, 5-lipoxygenase inhibitory activity, lipid peroxide production inhibitory activity, PPAR activating activity, anti-osteoporosis activity, leukotriene antagonizing activity, adipogenesis promoting effect, cancer cell proliferation inhibitory activity, calcium antagonizing activity, and the like. These 6-substituted-1-methyl-1-H-benzimidazole derivatives are known to be synthesized by condensation of 4-substituted-$N^2$-methylbenzene-1,2-diamines in which an N-methylamino group is protected and corresponding carboxylic acid derivatives and followed by deprotection and intramolecular dehydration (for example, see Patent Literatures 1 and 2).

4-Substituted-$N^2$-methylbenzene-1,2-diamines in which an N-methylamino group is protected can be synthesized from, for example, N-(5-substituted-2-nitrophenyl)-N-methylamines.

As a procedure for the preparation of N-(5-substituted-2-nitrophenyl)-N-methylamines, the preparation procedure by substituting a halogen atom of N-(5-halogeno-2-nitrophenyl)-N-methylamines with a nucleophilic reagent in the presence or absence of a base has been known (non patent literature 1). As a procedure for the preparation of the N-(5-halogeno-2-nitrophenyl)-N-methylamines used as the starting material in the above-mentioned preparation procedure, for example, the procedure for the preparation of N-(5-chloro-2-nitrophenyl)-N-methylamine by substituting a chlorine atom at the 2-position of 2,4-dichloronitrobenzene with methylamine has been known (patent literature 3). Since these N-(5-substituted-2-nitrophenyl)-N-methylamines are used as the manufacturing materials for the preparation of the 6-substituted-1-methyl-1-H-benzimidazole derivatives having high pharmaceutical activity, a preparation procedure for such N-(5-substituted-2-nitrophenyl)-N-methylamines, which is industrially more practical and additionally suitable for a large scale synthesis compared to the conventional procedure, has been desired to be developed.

Furthermore, as a procedure for the preparation of the 6-substituted-1-methyl-1-H-benzimidazole derivatives from the N-(5-substituted-2-nitrophenyl)-N-methylamines prepared by the above-mentioned reaction, the preparation procedure from N-(5-substituted-2-aminophenyl)-N-methylamines in which a methylamino group is protected, which can be prepared by reducing N-(5-substituted-2-nitrophenyl)-N-methylamines in which a methylamino group is protected previously, has been known (see patent literature 2), but a more efficient procedure for the preparation of the 6-substituted-1-methyl-1-H-benzimidazole derivatives by a shorter process has been desired to be developed.

[Patent Literature 1] Japanese Patent Publication (Kokai) Number Hei 9-295970

[Patent Literature 2] Japanese Patent Publication (Kokai) Number Hei 11-193276

[Patent Literature 3] European Patent Application No. 385850

[Non patent Literature 1] Journal of Medicinal Chemistry (USA) Vol. 39, p. 3971-3979 (1996)

DISCLOSURE OF THE INVENTION

Subject to be Solved by the Invention

The inventors of the present invention have diligently investigated various procedures for the preparation of 6-substituted-1-methyl-1-H-benzimidazole derivatives (I) and N-(5-substituted-2-nitrophenyl)-N-methylamines (IIa) which are new key intermediates in the preparation of the 6-substituted-1-methyl-1-H-benzimidazole derivatives (I) and derivatives thereof, and discovered a procedure for the preparation of N-(5-substituted-2-nitrophenyl)-N-methylamines (IIa) in high yield at high purity, and additionally a procedure for the preparation of N-(5-substituted-2-nitrophenyl)-N-methylamines (II) by a one-pot reaction via N-(5-chloro-2-nitrophenyl)-N-methylamine prepared by reacting 2,4-dichloronitrobenzene with methylamine in an aprotic solvent, and furthermore an efficient procedure for the preparation of the desired 6-substituted-1-methyl-1-H-benzimidazole derivatives (I) from N-(5-substituted-2-nitrophenyl)-N-methylamines (II) by shorter steps, and consequently, the inventors completed the present invention.

Measure to Solve the Subject

The present invention provides (1) a compound having the general formula (IIa) shown below,

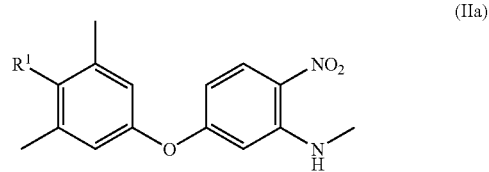

(IIa)

(wherein, $R^1$ represents a nitro group, an amino group or a t-butoxycarbonylamino group), (2) a compound having the general formula (III) shown below,

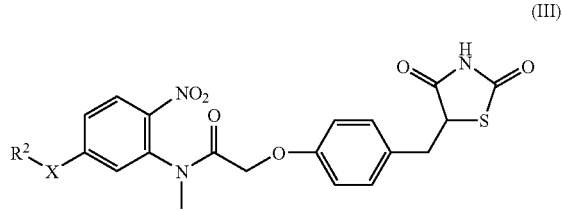

(III)

[wherein

R² represents a hydrogen atom, a $C_1$-$C_6$ alkyl group which may optionally be substituted with from 1 to 5 substituents selected from Substituent group α, a $C_3$-$C_6$ cycloalkyl group which may optionally be substituted with from 1 to 5 substituents selected from the group consisting of Substituent group α, a $C_1$-$C_6$ alkyl group and a halomethyl group, a phenyl group which may optionally be substituted with from 1 to 5 substituents selected from the group consisting of Substituent group α, a $C_1$-$C_6$ alkyl group and a halomethyl group, or a 5- or 6-membered heterocyclic group which may optionally be substituted with from 1 to 5 substituents selected from the group consisting of Substituent group α, a $C_1$-$C_6$ alkyl group and a halomethyl group (said heterocyclic group contains from 1 to 4 hetero atoms selected from the group consisting of a nitrogen atom, an oxygen atom and a sulfur atom), and X represents an oxygen atom, a sulfur atom or a nitrogen atom (said nitrogen atom may optionally be substituted with substituent(s) selected from the group consisting of a hydrogen atom, a $C_1$-$C_6$ alkyl group, a $C_1$-$C_6$ alkylcarbonyl group, a $C_6$-$C_{10}$ arylcarbonyl group, a $C_1$-$C_6$ alkylsulfonyl group and a $C_6$-$C_{10}$ arylsulfonyl group);

Substituent group α represents a $C_3$-$C_6$ cycloalkyl group, a $C_2$-$C_6$ alkenyl group, a $C_2$-$C_6$ alkynyl group, a $C_6$-$C_{10}$ aryl group, a carboxyl group, a formyl group, a $C_1$-$C_6$ alkylcarbonyl group, a $C_6$-$C_{10}$ arylcarbonyl group, a $C_1$-$C_6$ alkyloxycarbonyl group, a $C_6$-$C_{10}$ aryloxycarbonyl group, a carbamoyl group, an N—$C_1$-$C_6$ alkylcarbamoyl group, an N,N-di($C_1$-$C_6$ alkyl)carbamoyl group, a hydroxyl group, a $C_1$-$C_6$ alkoxy group, a $C_6$-$C_{10}$ aryloxy group, a $C_1$-$C_6$ alkylcarbonyloxy group, a $C_6$-$C_{10}$ arylcarbonyloxy group, an amino group, a $C_1$-$C_6$ alkylamino group, a di($C_1$-$C_6$ alkyl)amino group, a $C_6$-$C_{10}$ arylamino group, a di($C_6$-$C_{10}$ aryl)amino group, a mercapto group, a $C_1$-$C_6$ alkylthio group, a $C_6$-$C_{10}$ arylthio group, a $C_1$-$C_6$ alkylsulfinyl group, a $C_6$-$C_{10}$ arylsulfinyl group, a $C_1$-$C_6$ alkylsulfonyl group, a $C_6$-$C_{10}$ arylsulfonyl group, a sulfonic acid group, a halogen atom, a nitro group and a cyano group], (3) a compound according to (2) described above, wherein R² represents a $C_1$-$C_6$ alkyl group or a phenyl group which may optionally be substituted with from 1 to 3 substituents selected from the group consisting of Substituent group α, a $C_1$-$C_6$ alkyl group, and a halomethyl group (said Substituent group α represents an amino group, a $C_1$-$C_6$ alkylamino group, or a halogen atom), and X represents an oxygen atom, (4) a method for the preparation of a compound having the following general formula (I) or a pharmaceutically acceptable salt thereof, which is characterized by reduction of the nitro group of a compound having the following general formula (III), followed by intramolecular dehydration condensation, (I)

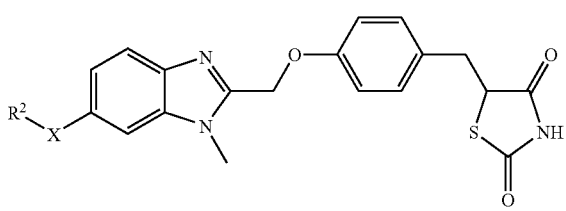

[wherein, R² and X have the same meanings as those indicated in (2) described above], (III)

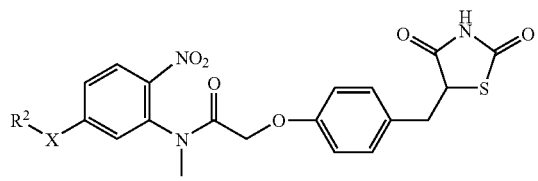

[wherein, R² and X have the same meanings as those indicated in (2) described above], (5) a method for the preparation of a compound according to (4) described above, wherein R² represents a $C_1$-$C_6$ alkyl group or a phenyl group which may optionally be substituted with from 1 to 3 substituents selected from the group consisting of Substituent group α, a $C_1$-$C_6$ alkyl group, and a halomethyl group (said Substituent group α represents an amino group, a $C_1$-$C_6$ alkylamino group, or a halogen atom), and X represents an oxygen atom, (6) a method for the preparation of a compound having the following general formula (III), which is characterized by condensation of a compound having the following general formula (II) and 4-[(2,4-dioxothiazolidin-5-yl)methyl]phenoxyacetic acid, (II)

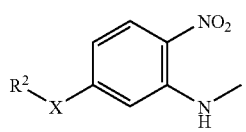

[wherein, R² and X have the same meanings as those indicated in (2) described above]

(III)

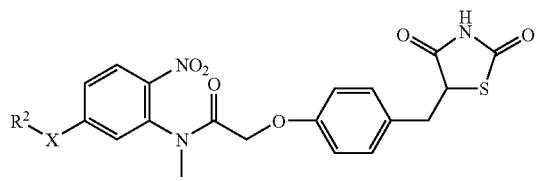

[wherein, R² and X have the same meanings as those indicated in (2) described above]

(7) a method for the preparation of a compound according to (6) described above, wherein R² represents a $C_1$-$C_6$ alkyl group or a phenyl group which may optionally be substituted with from 1 to 3 substituents selected from the group consisting of Substituent group α, a $C_1$-$C_6$ alkyl group, and a halomethyl group (said Substituent group α represents an amino group, a $C_1$-$C_6$ alkylamino group, or a halogen atom), and X represents an oxygen atom, (8) a method for the preparation of a compound having the following general formula (II), which is characterized by preparation of N-(5-chloro-2-nitrophenyl)-N-methylamine by reacting 2,4-dichloronitrobenzene with methylamine, followed by reaction of the resulting N-(5-chloro-2-nitrophenyl)-N-methylamine without isolation with a compound having the general formula of R²—X—H [wherein, R² and X have the same meanings as those indicated in (2) described above] in the presence of a base,

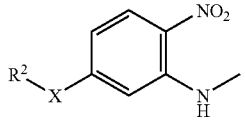

(II)

[wherein, $R^2$ and X have the same meanings as those indicated hereinbefore], (9) a method for the preparation of a compound according to (8) described above, wherein $R^2$ represents a $C_1$-$C_6$ alkyl group or a phenyl group which may optionally be substituted with from 1 to 3 substituents selected from the group consisting of Substituent group α, a $C_1$-$C_6$ alkyl group and a halomethyl group (said Substituent group α represents an amino group, a $C_1$-$C_6$ alkylamino group, or a halogen atom), and X represents an oxygen atom,

(10) a method for the preparation of a compound having the general formula (IIa) indicated in (1) described above, which is characterized by reacting N-(5-chloro-2-nitrophenyl)-N-methylamine with a compound having the following general formula (V) in the presence of a base in an inert solvent,

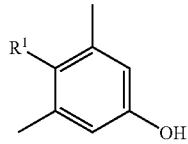

(V)

(wherein, $R^1$ represents a nitro group, an amino group, or a t-butoxycarbonylamino group),

(11) a method for the preparation of a compound having the general formula (IIa) indicated in (1) described above according to (10) described above, which is characterized by degassing of the inert solvent employed,

(12) a method for the preparation of a compound having the general formula (IIa) indicated in (1) described above according to (10) or (11) described above, which is characterized by addition of an antioxidant, and

(13) a method for the preparation of a compound having the general formula (IIa) indicated in (1) described above according to (12) described above, wherein the antioxidant employed is 2,6-di-t-butyl-4-methylphenol.

In the present invention, the "halogen atom" can be a fluorine, chlorine, bromine or iodine atom, and said atom in the definition of Substituent group α is preferably a fluorine or chlorine atom.

In the present invention, the "$C_1$-$C_6$ alkyl group" can be a straight or branched alkyl group having from 1 to 6 carbon atoms, and is, for example, a methyl, ethyl, propyl, isopropyl, butyl, isobutyl, s-butyl, t-butyl, pentyl, isopentyl, s-pentyl, t-pentyl, neopentyl, or hexyl group. Said group in the definition of $R^2$ is preferably a methyl, ethyl, propyl, isopropyl, butyl, isobutyl, s-butyl, or t-butyl group, and more preferably a methyl, ethyl, propyl, isopropyl, butyl, or isobutyl group. Said group in the definition of the substituent of the nitrogen atom when X represents a nitrogen atom is preferably a methyl, ethyl, propyl, or isopropyl group, and more preferably a methyl or ethyl group.

In the present invention, the "halomethyl group" can be a methyl group substituted with from 1 to 3 of the "halogen atoms" described above, and is, for example, a fluoromethyl, difluoromethyl, trifluoromethyl, dichloromethyl, or trichloromethyl group. As the substituent of a $C_3$-$C_6$-cycloalkyl group, a phenyl group, or a 5- or 6-membered heterocyclic group in the definition of $R^2$, a fluoromethyl, difluoromethyl, trifluoromethyl, or trichloromethyl group is preferred, and a trifluoromethyl group is more preferred.

In the present invention, the "$C_2$-$C_6$ alkenyl group" can be a straight or branched alkenyl group having from 2 to 6 carbon atoms, and is, for example, an ethenyl, 1-propenyl, 3-propenyl (or allyl), 2-methylpropen-1-yl, 2-methylpropen-3-yl (or methallyl), 1-buten-1-yl, 1-buten-2-yl, 1-buten-3-yl, 1-buten-4-yl, 2-buten-1-yl, 2-buten-2-yl, 2-methyl-1-buten-1-yl, 2-methyl-1-buten-3-yl, 2-methyl-1-buten-4-yl, 3-methyl-2-buten-2-yl, 2-ethyl-1-buten-1-yl, 2,3-dimethyl-2-buten-1-yl, 1-penten-1-yl, 1-penten-2-yl, 1-penten-3-yl, 1-penten-4-yl, 1-penten-5-yl, 2-penten-1-yl, 2-penten-2-yl, 2-penten-3-yl, 2-penten-4-yl, 2-penten-5-yl, 2-methyl-1-penten-1-yl, 3-methyl-2-penten-1-yl, 3-methyl-2-penten-2-yl, 2-ethyl-1-penten-1-yl, 3-ethyl-2-penten-1-yl, 3-ethyl-2-penten-2-yl, 1-hexen-1-yl, 1-hexen-2-yl, 2-hexen-1-yl, or 2-hexen-2-yl group. Said group in the definition of Substitutent group α is preferably a straight or branched alkenyl group having from 2 to 5 carbon atoms, and more preferably an ethenyl, 2-propenyl, or 3-propenyl group.

In the present invention, the "$C_2$-$C_6$ alkynyl group" can be a straight or branched alkynyl group having from 2 to 6 carbon atoms, and is, for example, an ethynyl, 1-propynyl, 3-propynyl (or propargyl), 1-butyn-1-yl, 1-butyn-3-yl, 1-butyn-4-yl, 2-butyn-1-yl, 1-pentyn-1-yl, 2-pentyn-1-yl, 3-methyl-1-pentyn-1-yl, 1-hexyn-1-yl, or 2-hexyn-1-yl group. Said group in the definition of Substitutent group α is preferably a straight or branched alkynyl group having from 2 to 5 carbon atoms, and more preferably an ethynyl, 1-propynyl, or 3-propynyl group.

In the present invention, the "$C_3$-$C_6$ cycloalkyl group" can be a 3- to 6-membered saturated cyclic hydrocarbon group, and is, for example, a cyclopropyl, cyclobutyl, cyclopentyl, or cylohexyl group.

Furthermore, the "$C_3$-$C_6$ cycloalkyl group" in the definition of $R^2$ may optionally be substituted with a $C_1$-$C_6$ alkyl group, and said group including such optionally substituted $C_3$-$C_6$ cycloalkyl groups in the definition of $R^2$ is preferably a cyclopropyl, 1-methylcyclopropyl, 2,2-dimethylcyclopropyl, cyclobutyl, 3,3-dimethylcyclobutyl, cyclopentyl, or cyclohexyl group. Said group in the definition of Substituent group α is preferably a cyclopropyl, cyclobutyl, cyclopentyl, or cyclohexyl group.

In the present invention, the "$C_6$-$C_{10}$ aryl group" can be an aromatic hydrocarbon having from 6 to 10 carbon atoms, and is, for example, a phenyl, indenyl, or naphthyl group. Said group in the definition of Substituent group α is preferably a phenyl group.

In the present invention, the "5- or 6-membered heterocyclic group" "including from 1 to 4 of the same or different hetero atoms selected from the group consisting of a nitrogen atom, an oxygen atom, and a sulfur atom" is, for example, 1H-pyrrol-2-yl, 1H-pyrrol-3-yl, 2-furyl, 3-furyl, 2-thienyl, 3-thienyl, 1H-pyrazol-3-yl, 1H-pyrazol-4-yl, 1H-imidazol-2-yl, 1H-imidazol-4-yl, 3-isoxazolyl, 4-isoxazolyl, 5-isoxazolyl, 2-oxazolyl, 4-oxazolyl, 5-oxazolyl, 3-isothiazolyl, 4-isothiazolyl, 5-isothiazolyl, 2-thiazolyl, 4-thiazolyl, 5-thiazolyl, 1H-1,2,3-triazol-4-yl, 1H-1,2,3-triazol-5-yl, 2H-1,2,3-triazol-4-yl, 1,2,4-oxadiazol-3-yl, 1,2,4-oxadiazol-5-yl, 1,2,4-thiadiazol-3-yl, 1,2,4-thiadiazol-5-yl, 2-pyridyl, 3-pyridyl, 4-pyridyl, 3-pyridazyl, 4-pyridazyl, 2-pyrimidyl, 4-pyrimidyl, 5-pyrimidyl, 2-pyrazyl, 1,2,4-triazin-3-yl, 1,2,4-triazin-4-yl, 1,2,4-triazin-5-yl, 1,2,4-triazin-6-yl, or 1,3,5-triazin-2-yl group.

Said group in the definition of $R^2$ is preferably 2-furyl, 3-furyl, 2-thienyl, 3-thienyl, 3-isoxazolyl, 4-isoxazolyl, 5-isoxazolyl, 2-oxazolyl, 4-oxazolyl, 5-oxazolyl, 3-isothiazolyl, 4-isothiazolyl, 5-isothiazolyl, 2-thiazolyl, 4-thiazolyl, 5-thiazolyl, 2-pyridyl, 3-pyridyl, 4-pyridyl, 3-pyridazyl, 4-pyridazyl, 2-pyrimidyl, 4-pyrimidyl, 5-pyrimidyl, 2-pyrazyl, or 1,3,5-triazin-2-yl group, and more preferably 2-furyl, 3-furyl, 2-thienyl, 3-thienyl, 3-isoxazolyl, 4-isoxazolyl, 5-isoxazolyl, 2-oxazolyl, 4-oxazolyl, 5-oxazolyl, 3-isothiazolyl, 4-isothiazolyl, 5-isothiazolyl, 2-thiazolyl, 4-thiazolyl, 5-thiazolyl, 2-pyridyl, 3-pyridyl, 4-pyridyl, 3-pyridazyl, 4-pyridazyl, 2-pyrimidyl, 4-pyrimidyl, 5-pyrimidyl, or 1,3,5-triazin-2-yl group.

In the present invention, the "$C_1$-$C_6$ alkoxy group" is a group wherein the "$C_1$-$C_6$ alkyl group" described hereinbefore is bonded to an oxygen atom, and can be, for example, a straight or branched chain alkoxy group having from 1 to 6 carbon atoms such as a methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, or 2,3-dimethylbutoxy group. Said group in the definition of Substitutent group α is preferably a methoxy group.

In the present invention, the "$C_6$-$C_{10}$ aryloxy group" is a group wherein the "$C_6$-$C_{10}$ aryl group" described hereinbefore is bonded to an oxygen atom, and is, for example, a phenoxy, α-naphthaleneoxy, or β-naphthaleneoxy group. Said group in the definition of Substitutent group α is preferably a phenoxy group.

In the present invention, the "$C_1$-$C_6$ alkylcarbonyl group" is a group wherein an aliphatic hydrocarbon group having from 1 to 6 carbon atoms is bonded to a carbonyl group, and is, for example, an acetyl, propionyl, butyryl, isobutyryl, pentanoyl, pivaloyl, valeryl, or isovaleryl group.

Additionally, the "$C_1$-$C_6$ alkylcarbonyl group" described above may optionally be substituted with a halogen atom or a $C_1$-$C_6$ alkoxy group, and furthermore the $C_1$-$C_6$ alkyl group may contain unsaturated bond(s). Such group is, for example, a halogenated alkylcarbonyl group such as a chloroacetyl, dichloroacetyl, trichloroacetyl, or trifluoroacetyl group; a $C_1$-$C_6$ alkoxyalkylcarbonyl group such as a methoxyacetyl group; or an unsaturated alkylcarbonyl group such as an (E)-2-methyl-2-butenoyl group. Said group as the substituent of the nitrogen atom when X represents a nitrogen atom and in the definition of Substituent group α is preferably an acetyl or propionyl group, and more preferably an acetyl group.

In the present invention, the "$C_6$-$C_{10}$ arylcarbonyl group" is a group wherein the "$C_6$-$C_{10}$ aryl group" described hereinbefore is bonded to a carbonyl group, and can be, for example, an aromatic acyl group consisting of an arylcarbonyl group such as a benzoyl, α-naphthoyl, or β-naphthoyl group; or a lower alkylated arylcarbonyl group such as a 2,4,6-trimethylbenzoyl, or 4-toluoyl group. Said group as the substituent of the nitrogen atom when X represents a nitrogen atom and in the definition of Substituent group α is preferably a benzoyl group.

In the present invention, the "$C_1$-$C_6$ alkylcarbonyloxy group" is a group wherein an aliphatic hydrocarbon group having from 1 to 6 carbon atoms or a hydrogen atom is bonded to a carbonyloxy group, and is, for example, a formyloxy, acetyloxy, propionyloxy, butyryloxy, isobutyryloxy, pentanoyloxy, pivaloyloxy, valeryloxy, or isovaleryloxy group.

Additionally, the "$C_1$-$C_6$ alkylcarbonyloxy group" described above may optionally be substituted with a halogen atom or a $C_1$-$C_6$ alkoxy group, and furthermore the $C_1$-$C_6$ alkyl group may contain unsaturated bond(s). Such group is, for example, a halogenated alkylcarbonyloxy group such as a chloroacetyloxy, dichloroacetyloxy, trichloroacetyloxy, or trifluoroacetyloxy group; a $C_1$-$C_6$ alkoxyalkylcarbonyloxy group such as a methoxyacetyloxy group; or an unsaturated alkylcarbonyloxy group such as an (E)-2-methyl-2-butenoyloxy group. Said group in the definition of Substituent group α is preferably a non-substituted $C_1$-$C_4$-alkylcarbonyloxy group, and more preferably a formyloxy or acetyloxy group.

In the present invention, the "$C_6$-$C_{10}$ arylcarbonyloxy group" is a group wherein the "$C_6$-$C_{10}$ aryl group" described hereinbefore is bonded to a carbonyloxy group, and can be, for example, a benzoyloxy, α-naphthoyloxy, or α-naphthoyloxy group.

Additionally, the "$C_6$-$C_{10}$ arylcarbonyloxy group" described above may optionally be substituted with a $C_1$-$C_6$ alkyl group, and such group is, for example, a $C_1$-$C_6$ alkylated arylcarbonyloxy group such as a 2,4,6-trimethylbenzoyloxy or 4-toluoyloxy group. Said group in the definition of Substituent group α is preferably a benzoyloxy group.

In the present invention, the "$C_1$-$C_6$ alkylsulfonyl group" is a group wherein the "$C_1$-$C_6$ alkyl group" described hereinbefore is bonded to a sulfonyl group, and can be, for example, a straight or branched chain alkanesulfonyl group having from 1 to 6 carbon atoms such as a methanesulfonyl, ethanesulfonyl, n-propanesulfonyl, isopropanesulfonyl, n-butanesulfonyl, isobutanesulfonyl, s-butanesulfonyl, tert-butanesulfonyl, n-pentanesulfonyl, isopentanesulfonyl, 2-methylbutanesulfonyl, neopentanesulfonyl, n-hexanesulfonyl, 4-methylpentanesulfonyl, 3-methylpentanesulfonyl, 2-methylpentanesulfonyl, 3,3-dimethylbutanesulfonyl, 2,2-dimethylbutanesulfonyl, 1,1-dimethylbutanesulfonyl, 1,2-dimethylbutanesulfonyl, 1,3-dimethylbutanesulfonyl, or 2,3-dimethylbutanesulfonyl group. Said group in the definition of Substituent group α is preferably a straight or branched alkanesulfonyl group having from 1 to 4 carbon atoms, and more preferably a methanesulfonyl group. Said group as the substituent of the nitrogen atom when X represents a nitrogen atom is preferably a methanesulfonyl group.

In the present invention, the "$C_6$-$C_{10}$ arylsulfonyl group" is a group wherein the "$C_6$-$C_{10}$ aryl group" described hereinbefore is bonded to a sulfonyl group, and can be, for example, a benzenesulfonyl, p-toluenesulfonyl, α-naphthalenesulfonyl, or β-naphthalenesulfonyl group. Said group in the definition of Substituent group α is preferably a benzenesulfonyl group. Said group as the substituent of the nitrogen atom when X represents a nitrogen atom is preferably a benzenesulfonyl, or p-toluenesulfonyl group.

In the present invention, the "$C_1$-$C_6$ alkoxycarbonyl group" is a group wherein the "$C_1$-$C_6$ alkoxy group" described hereinbefore is bonded to a carbonyl group, and can be, for example, a straight or branched chain alkoxycarbonyl group having from 1 to 6 carbon atoms such as a methoxycarbonyl, ethoxycarbonyl, n-propoxycarbonyl, isopropoxycarbonyl, n-butoxycarbonyl, isobutoxycarbonyl, s-butoxycarbonyl, tert-butoxycarbonyl, n-pentoxycarbonyl, isopentoxycarbonyl, 2-methylbutoxycarbonyl, neopentoxycarbonyl, n-hexyloxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, or 2,3-dimethylbutoxycarbonyl group. Said group in the definition of Substitutent group α is preferably a tert-butoxycarbonyl or methoxycarbonyl group, and more preferably tert-butoxycarbonyl group.

In the present invention, the "$C_6$-$C_{10}$ aryloxycarbonyl group" is a group wherein the "$C_6$-$C_{10}$ aryloxy group" described hereinbefore is bonded to a carbonyl group, and is, for example, a phenoxycarbonyl, α-naphthalenenoxycarbonyl, or β-naphthaleneoxycarbonyl group. Said group in the definition of Substitutent group α is preferably a phenoxycarbonyl group.

In the present invention, the "N—$C_1$-$C_6$ alkylcarbamoyl group" is a group wherein the "$C_1$-$C_6$ alkyl group" described hereinbefore is bonded to the nitrogen atom of a carbamoyl group, and can be, for example, a N-methylcarbamoyl, N—ethylcarbamoyl, N-propylcarbamoyl, N-isopropylcarbamoyl, N-butylcarbamoyl, N-isobutylcarbamoyl, N-s-butylcarbamoyl, N-t-butylcarbamoyl, N-pentylcarbamoyl, N-isopentylcarbamoyl, N-s-pentylcarbamoyl, N-t-pentylcarbamoyl, N-neopentylcarbamoyl, or N-hexylcarbamoyl group. Said group in the definition of Substitutent group α is preferably a N-methylcarbamoyl, or N-ethylcarbamoyl group.

In the present invention, the "N,N-di($C_1$-$C_6$ alkyl)carbamoyl group" is a group wherein two hydrogen atoms on the nitrogen atom of a carbamoyl group are substituted with two of the same or different "$C_1$-$C_6$ alkyl groups" described hereinbefore, and can be, for example, a N,N-dimethylcarbamoyl, N,N-diethylcarbamoyl, N,N-dipropylcarbamoyl, or N,N-diisopropylcarbamoyl group. Said group in the definition of Substitutent group α is preferably a N,N-dimethylcarbamoyl, or N,N-diethylcarbamoyl group.

In the present invention, the "$C_1$-$C_6$ alkylamino group" is a group wherein the "$C_1$-$C_6$ alkyl group" described hereinbefore is bonded to an amino group, and can be, for example, a methylamino, ethylamino, n-propylamino, isopropylamino, n-butylamino, isobutylamino, s-butylamino, tert-butylamino, n-pentylamino, isopentylamino, 2-methylbutylamino, neopentylamino, 1-ethylpropylamino, n-hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino, or 2-ethylbutylamino group. Said group in the definition of Substitutent group α is preferably a methylamino, ethylamino, propylamino, or isopropylamino group.

In the present invention, the "di($C_1$-$C_6$ alkyl)amino group" is a group wherein two hydrogen atoms of the amino group are substituted with two of the same or different "$C_1$-$C_6$ alkyl groups" described hereinbefore, and can be, for example, an N,N-dimethylamino, N,N-diethylamino, N,N-di(n-propyl)amino, N,N-diisopropylamino, N,N-di(n-butyl)amino, N,N-diisobutylamino, N,N-di(s-butyl)amino, N,N-di(tert-butyl)amino, N,N-di(n-pentyl)amino, N,N-diisopentylamino, N,N-di(2-methylbutyl)amino, N,N-dineopentylamino, N,N-di(1-ethylpropyl)amino, N,N-di(n-hexyl)amino, N,N-diisohexylamino, N,N-di(4-methylpentyl)amino, N,N-di(3-methylpentyl)amino, N,N-di(2-methylpentyl)amino, N,N-di(1-methylpentyl)amino, N,N-ethylmethylamino, or N,N-isopropylmethylamino group. Said group in the definition of Substitutent group α is preferably a N,N-dimethylamino group.

In the present invention, the "$C_6$-$C_{10}$ arylamino group" is a group wherein the "$C_6$-$C_{10}$ aryl group" described hereinbefore is bonded to an amino group, and can be, for example, a phenylamino, indenylamino, or naphthylamino group. Said group in the definition of Substitutent group α is preferably a phenylamino group.

In the present invention, the "di($C_6$-$C_{10}$ aryl)amino group" is a group wherein two hydrogen atoms of the amino group are substituted with two of the same or different "$C_6$-$C_{10}$ aryl groups" described hereinbefore, and can be, for example, a N,N-diphenyl group. Said group in the definition of Substitutent group α is preferably a N,N-diphenylamino group.

In the present invention, the "$C_1$-$C_6$ alkylthio group" is a group wherein a "$C_1$-$C_6$ alkyl group" described hereinbefore is bonded to a sulfur atom, and can be, for example, a methylthio, ethylthio, or t-butylthio group. Said group in the definition of Substitutent group α is preferably a methylthio group.

In the present invention, the "$C_6$-$C_{10}$ arylthio group" is a group wherein a "$C_6$-$C_{10}$ aryl group" described hereinbefore is bonded to a sulfur atom, and can be, for example, a phenylthio, α-naphthalenethio, or β-naphthalenethio group. Said group in the definition of Substitutent group α is preferably a phenylthio group.

In the present invention, the "$C_1$-$C_6$ alkylsulfinyl group" is a group wherein a "$C_1$-$C_6$ alkyl group" described hereinbefore is bonded to a sulfinyl group, and can be a methylsulfinyl, ethylsulfinyl, or t-butylsulfinyl group. Said group in the definition of Substitutent group α is preferably a methylsulfinyl group.

In the present invention, the "$C_6$-$C_{10}$ arylsulfinyl group" is a group wherein a "$C_6$-$C_{10}$ aryl group" is bonded to a sulfinyl group, and can be, for example, a phenylsulfinyl, α-naphthalenesulfinyl, or β-naphthalenesulfinyl group. Said group in the definition of Substitutent group α is preferably a phenylsulfinyl group.

When $R^2$ represents a "$C_1$-$C_6$ alkyl group" having substituents, the number of the substituents can be from 1 to 5, and is preferably from 1 to 3, and more preferably 1 or 2.

When $R^2$ represents a "$C_1$-$C_6$ alkyl group" having substituents and the number of the substituents is 2 or more than 2, these substituents may be the same or different from each other.

When $R^2$ represents a phenyl group or a heterocyclic group, each of which has substituents, the number of the substituents can be from 1 to 5, and is preferably from 1 to 4, and more preferably from 1 to 3.

When $R^2$ represents a phenyl group or a heterocyclic group, each of which has substituents, and the number of the substituents is 2 or more than 2, these substituents may be the same or different from each other.

$R^2$ is preferably a $C_1$-$C_6$ alkyl group or a phenyl group which may optionally be substituted with from 1 to 3 substituents selected from the group consisting of Substituent group α, a $C_1$-$C_6$ alkyl group and a halomethyl group (said Substituent group α represents an amino group, a $C_1$-$C_6$ alkylamino group or a halogen atom).

X is preferably an oxygen atom or a nitrogen atom (said nitrogen atom may optionally be substituted with a hydrogen atom, a $C_1$-$C_6$ alkylcarbonyl group or a $C_6$-$C_{10}$ arylcarbonyl group), and more preferably an oxygen atom.

The "pharmaceutically acceptable salt thereof" means a salt which, when the compounds of general formula (I) of the present invention have a basic group such as an amino group, can be prepared by reacting the compounds with an acid, and when the compounds of general formula (I) of the present invention have an acidic group such as a carboxyl group, can be prepared by reacting the compounds with a base.

The salt, when the compounds of general formula (I) have a basic group, is preferably an inorganic acid salt, for example, a hydrohalide such as hydrochloride, hydrobromide, or hydroiodide; inorganic acid salt such as a nitrate, a perchlorate, a sulfate, a phosphate or the like; an organic acid salt, for example, a lower alkanesulfonate such as methanesulfonate, trifluoromethanesulfonate, or ethanesulfonate, an arylsulfonate such as benzenesulfonate or p-toluenesulfonate, an acetate, a malate, a fumarate, a succinate, a citrate, an ascorbate, a tartrate, an oxalate, a maleate, or the like; or an amino acid salt such as glycine salt, lysine salt, arginine salt, ornithine salt, glutamic acid salt, or aspartic acid salt, and more preferably hydrochloride.

The salt, when the compounds of general formula (I) have an acidic group, is preferably a metal salt, for example, an alkali metal salt such as sodium salt, potassium salt, or lithium salt, an alkaline earth metal salt such as calcium salt or magnesium salt, an aluminum salt, an iron salt, or the like; an amine salt, for example, an inorganic amine salt such as ammonium salt, an organic amine salt such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, tris(hydroxymethyl) aminomethane salt, or the like; or an amino acid salt such as glycine salt, lysine salt, arginine salt, ornithine salt, glutamic acid salt, or aspartic acid salt.

As representative compounds of the present invention, the compounds shown in following Table can be listed, but the scope of the present invention should not be limited to these compounds.

The meaning of the abbreviations in the following Tables is shown below.

Boc: t-butoxycarbonyl group

Bu: n-butyl group cBu: cyclobutyl group chex: cyclohexyl group cPen: cyclopentyl group cPr: cyclopropyl group Et: ethyl group Hex: n-hexyl group iBu: isobutyl group iPr: isopropyl group Me: methyl group, neoPen: neopentyl group Pen: n-pentyl group Ph: phenyl group Pr: n-propyl group sBu: sec-butyl group tBu: tert-butyl group

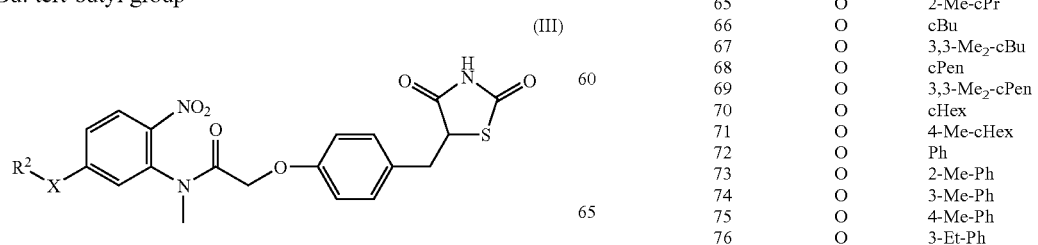

(III)

TABLE 2

| Compound No. | X | $R^2$ |
|---|---|---|
| 1 | O | Me |
| 2 | O | Et |
| 3 | O | Pr |
| 4 | O | iPr |
| 5 | O | Bu |
| 6 | O | iBu |
| 7 | O | sBu |
| 8 | O | tBu |
| 9 | O | Pen |
| 10 | O | neoPen |
| 11 | O | Hex |
| 12 | O | $CF_3CH_2-$ |
| 13 | O | $cPrCH_2-$ |
| 14 | O | $cBuCH_2-$ |
| 15 | O | $cPenCH_2-$ |
| 16 | O | $cHexCH_2-$ |
| 17 | O | $CH_2=CHCH_2-$ |
| 18 | O | $CH_2=CHC(Me)H-$ |
| 19 | O | $MeCH=CHCH_2-$ |
| 20 | O | $CH\equiv CCH_2-$ |
| 21 | O | $MeC\equiv CCH_2-$ |
| 22 | O | $CH\equiv CHC(Me)H-$ |
| 23 | O | $PhCH_2-$ |
| 24 | O | $PhC(Me)H-$ |
| 25 | O | $Ph-CH_2CH_2-$ |
| 26 | O | $HOCOCH_2-$ |
| 27 | O | $HCOCH_2-$ |
| 28 | O | $MeCOCH_2-$ |
| 29 | O | $PhCOCH_2-$ |
| 30 | O | $MeOCOCH_2-$ |
| 31 | O | $PhOCOCH_2-$ |
| 32 | O | $NH_2COCH_2-$ |
| 33 | O | $MeNHCOCH_2-$ |
| 34 | O | $Me_2NCOCH_2-$ |
| 35 | O | $HOCH_2-$ |
| 36 | O | $MeOCH_2-$ |
| 37 | O | $MeOCH_2CH_2-$ |
| 38 | O | $PhOCH_2-$ |
| 39 | O | $MeCOOCH_2-$ |
| 40 | O | $PhCOOCH_2-$ |
| 41 | O | $NH_2CH_2-$ |
| 42 | O | $MeNHCH_2-$ |
| 43 | O | $Me_2NCH_2-$ |
| 44 | O | $PhNHCH_2-$ |
| 45 | O | $Ph_2NCH_2-$ |
| 46 | O | $HSCH_2-$ |
| 47 | O | $MeSCH_2-$ |
| 48 | O | $MeSCH_2CH_2-$ |
| 49 | O | $PhSCH_2-$ |
| 50 | O | $MeSOCH_2-$ |
| 51 | O | $PhSOCH_2-$ |
| 52 | O | $MeSO_2CH_2-$ |
| 53 | O | $PhSO_2CH_2-$ |
| 54 | O | $HOSO_2CH_2-$ |
| 55 | O | $CH_2F-$ |
| 56 | O | $CHF_2-$ |
| 57 | O | $CF_3-$ |
| 58 | O | $CCl_3-$ |
| 59 | O | $NO_2CH_2-$ |
| 60 | O | $NO_2CH_2CH_2-$ |
| 61 | O | $NCCH_2-$ |
| 62 | O | $NCCH_2CH_2-$ |
| 63 | O | cPr |
| 64 | O | 1-Me-cPr |
| 65 | O | 2-Me-cPr |
| 66 | O | cBu |
| 67 | O | $3,3-Me_2-cBu$ |
| 68 | O | cPen |
| 69 | O | $3,3-Me_2-cPen$ |
| 70 | O | cHex |
| 71 | O | 4-Me-cHex |
| 72 | O | Ph |
| 73 | O | 2-Me-Ph |
| 74 | O | 3-Me-Ph |
| 75 | O | 4-Me-Ph |
| 76 | O | 3-Et-Ph |

TABLE 2-continued

| Compound No. | X | R² |
|---|---|---|
| 77 | O | 4-Et-Ph |
| 78 | O | 2-Pr-Ph |
| 79 | O | 4-Pr-Ph |
| 80 | O | 3-Bu-Ph |
| 81 | O | 4-Bu-Ph |
| 82 | O | 2-Pen-Ph |
| 83 | O | 4-Pen-Ph |
| 84 | O | 3-Hex-Ph |
| 85 | O | 4-Hex-Ph |
| 86 | O | 2-iPr-Ph |
| 87 | O | 4-iPr-Ph |
| 88 | O | 4-iBu-Ph |
| 89 | O | 4-sBu-Ph |
| 90 | O | 4-neoPen-Ph |
| 91 | O | 2-CH$_2$F-Ph |
| 92 | O | 4-CH$_2$F-Ph |
| 93 | O | 3-CHF$_2$-Ph |
| 94 | O | 4-CHF$_2$-Ph |
| 95 | O | 2-CF$_3$-Ph |
| 96 | O | 3-CF$_3$-Ph |
| 97 | O | 4-CF$_3$-Ph |
| 98 | O | 2-CCl$_3$-Ph |
| 99 | O | 3-CCl$_3$-Ph |
| 100 | O | 4-CCl$_3$-Ph |
| 101 | O | 3-CBr$_3$-Ph |
| 102 | O | 2-cPr-Ph |
| 103 | O | 3-cPr-Ph |
| 104 | O | 4-cPr-Ph |
| 105 | O | 2-cBu-Ph |
| 106 | O | 4-cBu-Ph |
| 107 | O | 3-cPen-Ph |
| 108 | O | 4-cPen-Ph |
| 109 | O | 2-cHex-Ph |
| 110 | O | 4-cHex-Ph |
| 111 | O | 2-CH$_2$=CH-Ph |
| 112 | O | 3-(CH$_2$=CH)-Ph |
| 113 | O | 3-(MeCH=CH)-Ph |
| 114 | O | 4-(CH$_2$=CHCH$_2$)-Ph |
| 115 | O | 4-{CH$_2$=CHCH(Me)}-Ph |
| 116 | O | 2-(CH≡C)-Ph |
| 117 | O | 4-(CH≡C)-Ph |
| 118 | O | 3-(MeC≡C)-Ph |
| 119 | O | 2-(CH≡CCH$_2$)-Ph |
| 120 | O | 4-(MeC≡CCH$_2$)-Ph |
| 121 | O | 2-Ph-Ph |
| 122 | O | 4-Ph-Ph |
| 123 | O | 2-HOCO-Ph |
| 124 | O | 3-HOCO-Ph |
| 125 | O | 4-HOCO-Ph |
| 126 | O | 2-HCO-Ph |
| 127 | O | 3-HCO-Ph |
| 128 | O | 4-HCO-Ph |
| 129 | O | 2-MeCO-Ph |
| 130 | O | 3-MeCO-Ph |
| 131 | O | 4-MeCO-Ph |
| 132 | O | 2-PhCO-Ph |
| 133 | O | 3-PhCO-Ph |
| 134 | O | 2-MeO-Ph |
| 135 | O | 3-MeO-Ph |
| 136 | O | 4-MeO-Ph |
| 137 | O | 2-EtO-Ph |
| 138 | O | 4-EtO-Ph |
| 139 | O | 2-PrO-Ph |
| 140 | O | 3-PrO-Ph |
| 141 | O | 4-iPrO-Ph |
| 142 | O | 3-BuO-Ph |
| 143 | O | 4-iBuO-Ph |
| 144 | O | 3-PenO-Ph |
| 145 | O | 4-neoPenO-Ph |
| 146 | O | 4-HexO-Ph |
| 147 | O | 2-PhO-Ph |
| 148 | O | 4-PhO-Ph |
| 149 | O | 2-NH$_2$CO-Ph |
| 150 | O | 3-NH$_2$CO-Ph |
| 151 | O | 3-MeNHCO-Ph |
| 152 | O | 3-Me$_2$NCO-Ph |
| 153 | O | 2-HO-Ph |
| 154 | O | 4-HO-Ph |
| 155 | O | 2-MeOCO-Ph |
| 156 | O | 4-MeOCO-Ph |
| 157 | O | 4-PhOCO-Ph |
| 158 | O | 3-MeCOO-Ph |
| 159 | O | 4-PhCOO-Ph |
| 160 | O | 2-NH$_2$-Ph |
| 161 | O | 4-NH$_2$-Ph |
| 162 | O | 2-MeNH-Ph |
| 163 | O | 3-MeNH-Ph |
| 164 | O | 4-MeNH-Ph |
| 165 | O | 3-EtNH-Ph |
| 166 | O | 4-PrNH-Ph |
| 167 | O | 3-PrNH-Ph |
| 168 | O | 2-iPrNH-Ph |
| 169 | O | 3-iPrNH-Ph |
| 170 | O | 4-iPrNH-Ph |
| 171 | O | 2-BuNH-Ph |
| 172 | O | 3-BuNH-Ph |
| 173 | O | 3-sBuH-Ph |
| 174 | O | 2-iBuNH-Ph |
| 175 | O | 3-iBuNH-Ph |
| 176 | O | 4-iBuNH-Ph |
| 177 | O | 3-PenNH-Ph |
| 178 | O | 3-neoPenNH-Ph |
| 179 | O | 4-neoPenNH-Ph |
| 180 | O | 3-HexNH-Ph |
| 181 | O | 4-Me$_2$N-Ph |
| 182 | O | 3-Et$_2$N-Ph |
| 183 | O | 3-Me$_2$N-Ph |
| 184 | O | 3-PhNH-Ph |
| 185 | O | 4-Ph$_2$N-Ph |
| 186 | O | 2-HS-Ph |
| 187 | O | 2-MeS-Ph |
| 188 | O | 2-PhS-Ph |
| 189 | O | 2-MeSO-Ph |
| 190 | O | 2-PhSO-Ph |
| 191 | O | 2-MeSO$_2$-Ph |
| 192 | O | 2-HOSO$_2$-Ph |
| 193 | O | 2-F-Ph |
| 194 | O | 3-F-Ph |
| 195 | O | 4-F-Ph |
| 196 | O | 2-Cl-Ph |
| 197 | O | 3-Cl-Ph |
| 198 | O | 4-Cl-Ph |
| 199 | O | 4-Br-Ph |
| 200 | O | 2-NO$_2$-Ph |
| 201 | O | 3-NO$_2$-Ph |
| 202 | O | 4-NO$_2$-Ph |
| 203 | O | 2-cyano-Ph |
| 204 | O | 3-cyano-Ph |
| 205 | O | 4-cyano-Ph |
| 206 | O | 2,4-Me$_2$-Ph |
| 207 | O | 3,5-Me$_2$-Ph |
| 208 | O | 3,5-Me$_2$-4-NH$_2$-Ph |
| 209 | O | 3,5-Me$_2$-4-MeNH-Ph |
| 210 | O | 3,5-Me$_2$-4-BocNH-Ph |
| 211 | O | 3,5-Me$_2$-4-NO$_2$-Ph |
| 212 | O | 3,5-Me$_2$-4-cyano-Ph |
| 213 | O | 2,4-F$_2$-Ph |
| 214 | O | 2,4-Cl$_2$-Ph |
| 215 | O | 2,3,4,5,6-F$_5$-Ph |
| 216 | O | 1H-1-Me-pyrrol-2-yll |
| 217 | O | 2-furyl |
| 218 | O | 2-thienyl |
| 219 | O | 1H-1-Me-pyrazol-3-yl |
| 220 | O | 1H-1-Me-imidazol-2-yl |
| 221 | O | 3-isooxazolyl |
| 222 | O | 2-oxazolyl |
| 223 | O | 3-isothiazolyl |
| 224 | O | 2-thiazolyl |
| 225 | O | 1H-1Me-1,2,3-triazol-4-yl |
| 226 | O | 1,2,4-oxadiazol-3-yl |
| 227 | O | 1,2,4-thiadiazole-3-yl |
| 228 | O | 2-pyridyl |

TABLE 2-continued

| Compound No. | X | R² |
|---|---|---|
| 229 | O | 3-pyridyl |
| 230 | O | 4-pyridyl |
| 231 | O | 3-pyridazinyl |
| 232 | O | 2-pyrimidinyl |
| 233 | O | 1,3,5-triazine-2-yl |
| 234 | S | Me |
| 235 | S | Et |
| 236 | S | Pr |
| 237 | S | iPr |
| 238 | S | Bu |
| 239 | S | iBu |
| 240 | S | sBu |
| 241 | S | tBu |
| 242 | S | Pen |
| 243 | S | neoPen |
| 244 | S | Hex |
| 245 | S | NH₂CH₂— |
| 246 | S | MeNHCH₂— |
| 247 | S | Me₂NCH₂— |
| 248 | S | cPr |
| 249 | S | 1-Me-cPr |
| 250 | S | 2-Me-cPr |
| 251 | S | cBu |
| 252 | S | 3,3-Me₂-cBu |
| 253 | S | cPen |
| 254 | S | 3,3-Me₂-cPen |
| 255 | S | cHex |
| 256 | S | 4-Me-cHex |
| 257 | S | Ph |
| 258 | S | 4-Me-Ph |
| 259 | S | 3,5-Me₂-Ph |
| 260 | S | 4-F-Ph |
| 261 | S | 3,5-F₂-Ph |
| 262 | S | 3-NH₂-Ph- |
| 263 | S | 4-NH₂-Ph- |
| 264 | S | 2-MeNH-Ph |
| 265 | S | 3-MeNH-Ph |
| 266 | S | 4-MeNH-Ph |
| 267 | S | 3-EtNH-Ph |
| 268 | S | 3-PrNH-Ph |
| 269 | S | 3-iPrNH-Ph |
| 270 | S | 3-BuNH-Ph |
| 271 | S | 3-iBuNH-Ph |
| 272 | S | 2-NO₂-Ph |
| 273 | S | 3-NO₂-Ph |
| 274 | S | 4-NO₂-Ph |
| 275 | S | 1H-1-Me-pyrrol-2-yl |
| 276 | S | 2-furyl |
| 277 | S | 2-thienyl |
| 278 | S | 1H-1-Me-pyrazol-3-yl |
| 279 | S | 1H-1-Me-imidazol-2-yl |
| 280 | S | 3-isooxazolyl |
| 281 | S | 2-oxazolyl |
| 282 | S | 3-isothiazolyl |
| 283 | S | 2-thiazolyl |
| 284 | S | 1H-1Me-1,2,3-triazol-4-yl |
| 285 | S | 1,2,4-oxadiazol-3-yl |
| 286 | S | 1,2,4-thiadiazole-3-yl |
| 287 | S | 2-pyridyl |
| 288 | S | 3-pyridyl |
| 289 | S | 4-pyridyl |
| 290 | S | 3-pyridazinyl |
| 291 | S | 2-pyrimidinyl |
| 292 | S | 1,3,5-triazine-2-yl |

Among the above compounds, preferred compounds are the compounds of Exemplification Compound Nos. 1-17, 21, 23, 28, 30, 32, 34, 36, 37, 38, 47, 49, 52, 57, 59, 61, 68, 70, 73, 75, 77, 87, 97, 113, 118, 120, 122, 130, 133, 136, 150, 152, 156, 158, 162, 163, 165-169, 172-175, 177, 180, 181, 184, 191, 193, 195, 196, 198, 202, 204, 205, 207-211, 212, 213, 221, 223, 234-236, 239, 241, 243, 247, 253, 257, 259, 260, 261, 263, 274, 282, 284, 287, 289, 290, and 291.

More preferred compounds are the compounds of Exemplification Compound Nos. 1, 2, 4, 30, 34, 37, 47, 68, 75, 136, 163, 165, 167, 169, 175, 184, 195, 202, 205, 207, 208, 209, 210, 211, 213, 257, 260, 282, and 291.

Even more preferred compounds are the compounds of Exemplification compound number 1: (2-{4-[2,4-dioxo-1,3-thiazolidin-5-yl]methyl}phenoxy}-N-(5-methoxy-2-nitrophenyl)-N-methylacetamide, Exemplification compound number 169: (2-{4-[2,4-dioxo-1,3-thiazolidin-5-yl]methyl}phenoxy)-N-[5-(3-isopropylaminophenoxy)-2-nitrophenyl]-N-methylacetamide, Exemplification compound number 208: (N-[5-(4-amino-3,5-dimethylphenoxy)-2-nitrophenyl]-2-{4-[2,4-dioxo-1,3-thiazolidin-5-yl]methyl}phenoxy)-N-methylacetamide, Exemplification compound number 210: (4-{3-[({4-[(2,4-dioxo-1,3-thiazolidin-5-yl)methoxy]phenoxy}acetyl)(methyl)amino]-4-nitrophenoxy}-2,6-dimethylphenylcarbamic acid t-butyl ester, and Exemplification compound number 211: (N-[5-(3,5-dimethyl-4-nitrophenoxy)-2-nitrophenyl]-2-{4-[2,4-dioxo-1,3-thiazolidin-5-yl]methyl}phenoxy)-N-methylacetamide.

Advantage of Invention

The present invention provides new intermediates (IIa) and (III) of the 6-substituted-1-methyl-1-H-benzimidazol derivatives (I) which are the known pharmaceutically active ingredients. Furthermore, the present invention provides a procedure for the preparation of N-(5-substituted-2-nitrophenyl)-N-methylamines (II), which are synthetic intermediates, in high yield at high purity, and additionally a preparation procedure suitable for the large scale synthesis of said intermediates (II). By using the preparation procedure of the present invention, it is possible to prepare conveniently the intermediates (II) in good yield from a starting compound by a one-pot reaction, and further, in the large scale synthesis, said intermediates can be prepared using inexpensive reagents in good yield at high purity by simple procedure(s).

Additionally, the 6-substituted-1-methyl-1-H-benzimidazol derivatives (I) can be prepared not via N-(5-substituted-2-aminophenyl)-N-methylamine which needs the protection reaction of a methylamino group in the conventional procedure, but can be prepared efficiently from N-(5-substituted-2-nitrophenyl)-N-methylamines (II) which can be prepared by the procedure of the present invention, without going via N-(5-substituted-2-aminophenyl)-N-methylamine, in a high yield by short steps without a protection reaction.

Best Mode for Carrying Out the Invention

Procedures for the preparation of compounds (I), (II), (IIa), and (III) of the present invention are described in detail hereinafter.

The compound (II) can be prepared, for example, according to the procedure described below.

The compound (IIa), a new synthetic intermediate, is a compound having the formula of a compound (II) wherein R² represents a phenyl group which may optionally be substituted with from 1 to 5 substituents selected from the group consisting of Substituent group α, a $C_1$-$C_6$ alkyl group, and a halomethyl group, and more specifically a compound having the formula of a compound (II) wherein R² represents a 4-substituted-3,4-dimethylphenyl-4-yl group, and is encompassed by compound (II). Compound (IIa) can be prepared according to the preparation procedure of a compound (II) shown below, but more specifically can be prepared by reacting N-(5-chloro-2-nitrophenyl)-N-methylamine with a hydroxyaryl derivative having the following general formula (V) in Step 2 described below, and this reaction process is particularly described hereinafter as Step 2a.

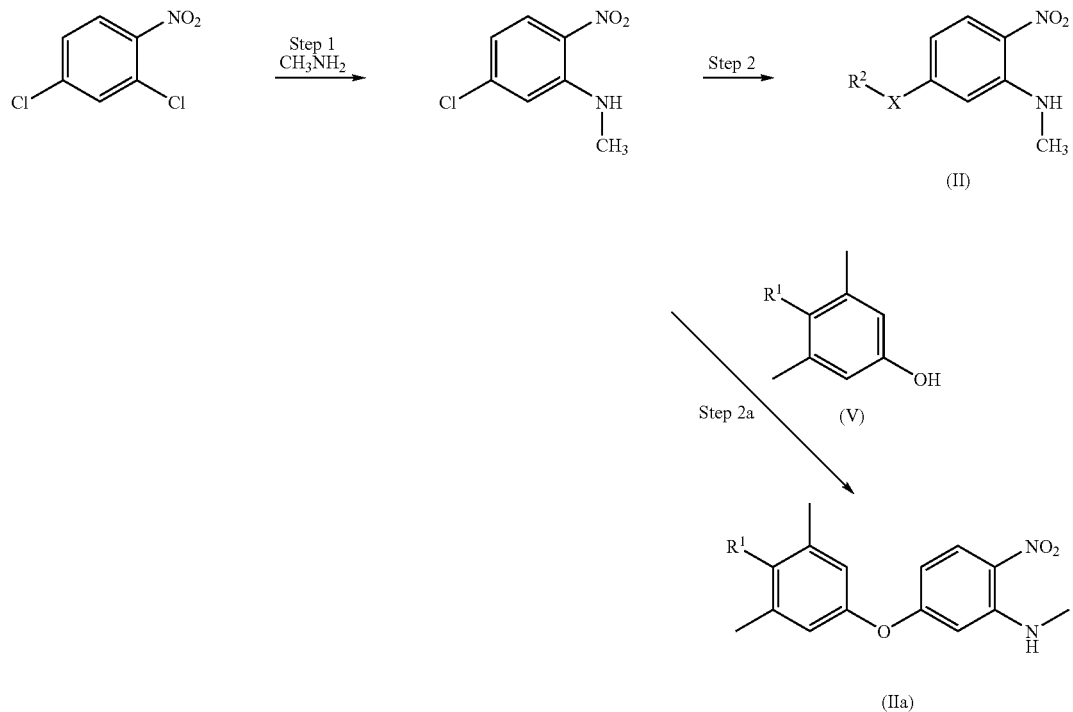

In the above reaction scheme and description hereinafter, $R^1$, $R^2$ and X have the same meanings as those indicated hereinbefore.

The procedures for the preparation of the present invention are comprised of Step 1, a process for the preparation of N-(5-chloro-2-nitrophenyl)-N-methylamine by reacting 2,4-dichloronitrobenzene with methylamine, and Step 2, a process for the preparation of a compound (II) by reacting N-(5-chloro-2-nitrophenyl)-N-methylamine without isolation from the reaction mixture obtained in Step 1 with water, an alcohol, a phenol, hydrogen sulfide, a mercaptan, ammonia, an amine or an amide. Furthermore, N-(5-chloro-2-nitrophenyl)-N-methylamine prepared in Step 1 can be isolated, for example, in accordance with the procedure described in patent literature 3, if necessary.

The processes of Step 1 and Step 2 are described in detail hereinafter.

(Step 1)

Step 1 is a process for the preparation of N-(5-chloro-2-nitrophenyl)-N-methylamine by reacting 2,4-dichloronitrobenzene with methylamine at an ordinary pressure in an inert solvent.

The inert solvent employed in this process is not particularly restricted provided that it dissolves the materials, 2,4-dichloronitrobenzene, methylamine and N-(5-chloro-2-nitrophenyl)-N-methylamine, at least to some extent and that it has no adverse effect on the reaction. Such a solvent can be, for example, an ether such as diethyl ether, diisopropyl ether, daibutyl ether, t-butylmethyl ether, cyclopropylmethyl ether, dimethyl cellosolve, tetrahydrofuran, dioxane, or the like; an amide such as dimethylformamide, dimethylacetamide, N,N-dimethylimidazolidinone, or hexamethylphosphoric triamide; a sulfoxide such as dimethyl sulfoxide, sulfolane, or the like; or a mixed solvent thereof, and is preferably an ether, an amide or a sulfoxide, and more preferably tetrahydrofuran, dimethylformamide, dimethylacetamide, or dimethyl sulfoxide.

Methylamine employed in this process can be added in the gaseous phase or as a solution. When methylamine is added as a solution, the solvent employed is not particularly restricted provided that it dissolves methylamine. Such a solvent can be, for example, water; an alcohol such as methanol, ethanol, propanol, isopropyl alcohol, butanol, isobutyl alcohol, t-butyl alcohol, methyl cellosolve, or the like; a hydrocarbon such as pentane, hexane, heptane, octane, isooctane, petroleum ether, cyclohexane, methylcyclohexane, ethylcyclohexane, benzene, toluene, xylene, mesitylene, or the like; an ether such as diethyl ether, diisobutyl ether, dibutyl ether, t-butylmethyl ether, cyclopropylmethyl ether, dimethyl cellosolve, tetrahydrofuran, dioxane, or the like; an amide such as dimethylformamide, dimethylacetamide, N,N-dimethylimidazolidinone, hexamethylphosphoric triamide, or the like; or a sulfoxide such as dimethyl sulfoxide, sulfolane, or the like, and is preferably water, an alcohol, an ether, an amide or a sulfoxide, and more preferably water, methanol, ethanol, tetrahydrofuran, dimethylformamide, dimethylacetamide, or dimethyl sulfoxide.

When a methylamine solution is used in this process, the concentration of the solution is not particularly restricted, but is usually from a 1% solution to a saturated solution, preferably from a 10% solution to a saturated solution, and more preferably from a 20% solution to a saturated solution.

The amount of methylamine employed in this process is not particularly restricted provided that it is more than 1 molar equivalent of the amount of compound 2,4-dichloronitrobenzene used, and is preferably from 1 to 10 molar equivalents, and more preferably from 3 to 6 molar equivalents.

The reaction temperature of this process is not particularly restricted, and is generally between 0° C. and refluxing temperature, preferably between room temperature and 120° C., and more preferably between 40° C. and 90° C.

The ordinary pressure in this process indicates atmospheric pressure, but the reaction is not affected even if the pressure is a little higher or lower than the ordinary pressure due to the structure of the reaction vessels. The pressure in this process is not particularly restricted, but it is generally between 0.5 and 10 atmospheric pressures, and preferably between 0.9 and 2 atmospheric pressures.

The reaction time of this process is not particularly restricted, and is generally from 15 minutes to 24 hours, preferably from 15 minutes to 6 hours, and more preferably between 30 minutes and 3 hours.

After completion of the reaction of this process, the reaction mixture obtained is used for Step 2 without any post-treatment.

(Step 2)

Following Step 1, Step 2 is carried out using N-(5-chloro-2-nitrophenyl)-N-methylamine obtained in Step 1 described above without isolation from the reaction mixture.

Step 2 is a process for the preparation of a compound (II) by reacting N-(5-chloro-2-nitrophenyl)-N-methylamine without isolation from the reaction mixture with water, an alcohol, a hydroxyaryl derivative, hydrogen sulfide, a mercaptan, ammonia, an amine or an amide in the presence of a base.

In this process, the inert solvent employed in Step 1 is used as it is.

The base employed in this process may be used directly for the reaction as a salt prepared previously by reacting with water, an alcohol, a hydroxyaryl derivative, hydrogen sulfide, a mercaptan, ammonia, an amine or an amide.

The amount of the base employed in this process is generally from 1 to 2 molar equivalents of the amount of water, an alcohol, a hydroxyaryl derivative, hydrogen sulfide, a mercaptan, ammonia, an amine or an amide employed, and is preferably from 1 to 1.6 molar equivalents, and more preferably 1.2 molar equivalents.

The alcohol employed in this process is not particularly restricted provided that it is a straight or branched chain $C_1$-$C_6$ alkyl alcohol which may optionally be substituted with substituent(s), and is, for example, methanol, ethanol, propanol, isopropyl alcohol, butanol, isobutyl alcohol, s-butyl alcohol, t-butyl alcohol, pentanol, isopentyl alcohol, s-pentyl alcohol, t-pentyl alcohol, neopentyl alcohol, hexanol, allyl alcohol, popargyl alcohol, benzyl alcohol, (pyridine-4-yl) methanol, 2-methoxyethanol, 2-methylthioethanol, 2,2,2-trifluoroethanol, 2-cyanoethanol, or the like, and preferably methanol, ethanol, propanol, isopropyl alcohol, butanol, isobutyl alcohol, s-butyl alcohol, t-butyl alcohol, allyl alcohol, popargyl alcohol, or benzyl alcohol.

The hydroxyaryl derivative employed in this process is not particularly restricted, and is, for example, phenol, 2-methylphenol, 4-methylphenol, 4-ethylphenol, 4-propylphenol, 3-isopropylphenol, 4-phenylphenol, 4-carboxyphenol, 4-formylphenol, 4-acetylphenol, 4-benzoylphenol, 4-methoxyphenol, 2-ethoxyphenol, 4-propoxyphenol, 3-isopropoxyphenol, 4-phenoxyphenol, 4-aminophenol, 2-(N-methylamino)phenol, 3-(N,N-dimethylamino)phenol, 3-(N-isopropylamino)phenol, 4-amino-3,5-dimethylphenol, 3-morpholinophenol, 4-(N-phenylamino)phenol, 4-(N,N-dimethylamino)phenol, 4-(N-methylcarbamoyl)phenol, 4-(N,N-dimethylcarbamoyl)phenol, 4-(methylthio)phenol, 2-(phenylthio)phenol, 3-(methylsulfinyl)phenol, 4-(phenylsulfinyl)phenol, 4-(methylsulfonyl)phenol, 3-(phenylsulfonyl)phenol, 3-hydroxybenzensulfonic acid, 2-fluorophenol, 3-fluorophenol, 4-fluorophenol, 3,5-difluorophenol, 2-chlorophenol, 4-chlorophenol, 2,4-dichlorophenol, 4-bromophenol, 3-nitrophenol, 3,5-dimethyl-4-nitrophenol, 2-cyanophenol, 3-cyanophenol, 4-cyanophenol, 2-hydroxypyridine (tautomer of 2-pyridone), 3-hydroxypyridine, or 4-hydroxypyridine, and preferably phenol, 4-methylphenol, 3-isopropylphenol, 3,5-dimethylphenol, 4-methoxyphenol, 3-isopropoxyphenol, 4-aminophenol, 2-(N-methylamino)phenol, 3-(N,N-dimethylamino)phenol, 3-(N-isopropylamino)phenol, 4-amino-3,5-dimethylphenol, 3-morpholinophenol, 4-(methylthio)phenol, 2-fluorophenol, 3-fluorophenol, 4-fluorophenol, 3,5-difluorophenol, 2-chlorophenol, 4-chlorophenol, 2,4-dichlorophenol, 4-bromophenol, 3-nitrophenol, 3,5-dimethyl-4-nitrophenol, 3-cyanophenol or 4-cyanophenol.

The mercaptan employed in this process is not particularly restricted, and is, for example, methyl mercaptan, ethyl mercaptan, propyl mercaptan, isopropyl mercaptan, butyl mercaptan, isobutyl mercaptan, s-butyl mercaptan, t-butyl mercaptan, pentyl mercaptan, isopentyl mercaptan, s-pentyl mercaptan, t-pentyl mercaptan, neopentyl mercaptan, hexyl mercaptan, allyl mercaptan, propargyl mercaptan, benzyl mercaptan, (pyridine-4-yl)methyl mercaptan, 2-methoxyethyl mercaptan, phenyl mercaptan, 2-methylphenyl mercaptan, 4-methylphenyl mercaptan, 4-ethylphenyl mercaptan, 4-propylphenyl mercaptan, 3-isopropylphenyl mercaptan, 4-phenylphenyl mercaptan, 4-carboxyphenyl mercaptan, 4-acetylphenyl mercaptan, 4-methoxyphenyl mercaptan, 2-ethoxyphenyl mercaptan, 4-propoxyphenyl mercaptan, 3-isopropxyphenyl mercaptan, 4-phenoxyphenyl mercaptan, 4-aminophenyl mercaptan, 2-(N-methylamino)phenyl mercaptan, 3-(N,N-dimethylamino)phenyl mercaptan, 3-(N-isopropylamino)phenyl mercaptan, 4-amino-3,5-dimethylphenyl mercaptan, 3-morpholinophenyl mercaptan, 4-(N-phenylamino)phenyl mercaptan, 4-(methylthio)phenyl mercaptan, 2-(phenylthio)phenyl mercaptan, 3-(methylsulfinyl)phenyl mercaptan, 4-(methylsulfonyl)phenyl mercaptan, 3-(phenylsulfonyl)phenyl mercaptan, 2-fluorophenyl mercaptan, 3-fluorophenyl mercaptan, 4-fluorophenyl mercaptan, 3,5-difluorophenyl mercaptan, 2-chlorophenyl mercaptan, 4-chlorophenyl mercaptan, 2,4-dichlorophenyl mercaptan, 3-nitrophenyl mercaptan, 3,5-dimethyl-4-nitrophenyl mercaptan, 2-cyanophenyl mercaptan, 3-cyanophenyl mercaptan, 4-cyanophenyl mercaptan, 2-pyridyl mercaptan (tautomer of 2-thiopyridone), 3-pyridyl mercaptan, or 4-pyridyl mercaptan, and preferably methyl mercaptan, ethyl mercaptan, propyl mercaptan, isopropyl mercaptan, butyl mercaptan, isobutyl mercaptan, t-butyl mercaptan, neopentyl mercaptan, allyl mercaptan, benzyl mercaptan, (pyridine-4-yl)methyl mercaptan, phenyl mercaptan, 4-methylphenyl mercaptan, 4-ethylphenyl mercaptan, 4-propylphenyl mercaptan, 3-isopropylphenyl mercaptan, 4-phenyl mercaptan, 4-carboxyphenyl mercaptan, 4-methoxyphenyl mercaptan, 3-isopropoxyphenyl mercaptan, 4-phenoxyphenyl mercaptan, 4-aminophenyl mercaptan, 2-(N-methylamino)phenyl mercaptan, 3-(N,N-dimethylamino)phenyl mercaptan, 3-(N-isopropylamino)phenyl mercaptan, 4-amino-3,5-dimethylphenyl mercaptan, 3-morpholinophenyl mercaptan, 4-(N-phenylamino)phenyl mercaptan, 4-(methylthio)phenyl mercaptan, 2-(phenylthio)phenyl mercaptan, 3-(methylsulfinyl)phenyl mercaptan, 4-(methylsulfonyl)phenyl mercaptan, 3-(phenylsulfonyl)phenyl mercaptan, 2-fluorophenyl mercaptan, 3-fluorophenyl mercaptan, 4-fluorophenyl mercaptan, 3,5-difluorophenyl mercaptan, 2-chlorophenyl mercaptan, 4-chlorophenyl mercaptan, 2,4-dichlorophenyl mercaptan, 3-nitrophenyl mercaptan, 3,5-dimethyl-4-nitrophenyl mercaptan, 2-cyanophenyl mercaptan, 3-cyanophenyl mercaptan, 4-cyanophenyl mercaptan, 2-pyridyl mercaptan (tautomer of 2-thiopyridone), 3-pyridyl mercaptan, or 4-pyridyl mercaptan.

The amine employed in this process is not particularly restricted, and is, for example, methylamine, ethylamine, propylamine, isopropylamine, butylamine, isobutylamine, s-butylamine, t-butylamine, pentylamine, isopentylamine, s-pentylamine, t-pentylamine, neopentylamine, hexylamine, allylamine, propargylamine, benzylamine, pyridine-4-yl-methylamine, 2-methoxyethylamine, phenylamine, 2-methylphenylamine, 4-methylphenylamine, 4-ethylphenylamine, 4-propylphenylamine, 3-isopropylphenylamine, 4-phenylamine, 4-carboxyphenylamine, 4-methoxyphenylamine, 2-ethoxyphenylamine, 4-propoxyphenylamine, 3-isopropoxyphenylamine, 4-phenoxylphenyamine, 2-(N-methylamino)phenylamine, 3-(N,N-dimethylamino)phenylamine, 3-(N-isopropylamino)phenylamine, 4-amino-3,5-dimethylphenylamine, 3-morpholinophenylamine, 4-(N-phenylamino)phenylamine, 4-(methylthio)phenylamine, 2-(phenylthio)phenylamine, 3-(methylsulfinyl)phenylamine, 4-(methylsulfonyl)phenylamine, 3-(phenylsulfonyl)phenylamine, 2-fluorophenylamine, 3-fluorophenylamine, 4-fluorophenylamine, 3,5-difluorophenylamine, 2-chlorophenylmine, 4-chlorophenylamine, 2,4-dichlorophenylamine, 3-nitrophenylamine, 3,5-dimethyl-4-nitrophenylamine, 2-cyanophenylamine, 3-cyanophenylamine, 4-cyanophenylamine, 2-pyridylamine, 3-pyridylamine, 4-pyridylamine, N,N-dimethylamine, N,N-diisopropylamine, pyrrolidine, morpholine, or N-methyl-N-phenylamine, and preferably methylamine, ethylamine, propylamine, isopropylamine, butylamine, isobutylamine, t-butylamine, neopentylamine, hexylamine, allylamine, benzylamine, (pyridine-4-yl)methylamine, phenylamine, 2-methylphenylamine, 4-methylphenylamine, 4-ethylphenylamine, 3-isopropylphenylamine, 4-phenylamine, 4-methoxyphenylamine, 2-ethoxyphenylamine, 3-isopropoxyphenylamine, 4-phenoxyphenyamine, 2-(N-methylamino)phenylamine, 3-(N,N-dimethylamino)phenylamine, 3-(N-isopropylamino)phenylamine, 4-amino-3,5-dimethylphenylamine, 3-morpholinophenylamine, 4-(N-phenylamino)phenylamine, 4-(methylthio)phenylamine, 2-(phenylthio)phenylamine, 3-(methylsulfinyl)phenylamine, 4-(methylsulfonyl)phenylamine, 2-fluorophenylamine, 3-fluorophenylamine, 4-fluorophenylamine, 3,5-difluorophenylamine, 2-chlorophenylamine, 4-chlorophenylamine, 2,4-dichlorophenylamine, 3-nitrophenylamine, 3,5-dimethyl-4-nitrophenylamine, 2-cyanophenylamine, 3-cyanophenyamine, 4-cyanophenylamine, 3-pyridylamine, 4-pyridylamine, N,N-dimethylamine, N,N-diisopropylamine, pyrrolidine, morpholine, or N-methyl-N-phenylamine.

The amide employed in this process is not particularly restricted, and is, for example, acetamide, benzamide, methanesulfonylamide, benzenesulfonylamide, N-methylacetamide, N-isopropylacetamide, N-phenylacetamide, N-methylbenzamide, N-methyl-methanesulfonylamide, N-butyl-methanesulfonylamide, or N-methylbenzenesulfonylamide, and preferably acetamide, benzamide, methanesulfonylamide, N-methylacetamide, N-isopropylacetamide, or N-methyl-methanesulfonylamide.

The reaction temperature of this process is not particularly restricted, and is generally between 0° C. and refluxing temperature, preferably between room temperature and 180° C., and more preferably between 40° C. and 150° C.

The reaction time of this process is not particularly restricted, and is generally from 15 minutes to 24 hours, preferably from 15 minutes to 6 hours, and more preferably between 30 minutes and 3 hours.

After completion of the reaction of this process or a post-treatment of the reaction mixture, the product compound (II) is isolated from the reaction mixture acidified, neutralized or alkalized depending on the physico-chemical properties of the product by a conventional procedure, for example, extraction, collection by filtration and the like. The isolated product can be used without any further treatment, or, if necessary, the isolated product is further purified before use by a conventional purification method such as distillation, re-crystallization, sublimation, partitioning, or chromatography.

Especially, in Step 2, the yield and purity of the desired compound (II) may be lowered by oxidizable impurities formed as by-products. In such cases, it can be possible to suppress the formation of these impurities by degassing of the inert solvent employed or addition of an antioxidant, or degassing of the inert solvent and addition of an antioxidant, and consequently, the desired compound (II) can be obtained in high yield at high purity by a simple procedure. Such an antioxidant is not particularly restricted provided that its anti-oxidation effect is confirmed, and is preferably 2,4-di-t-butyl-4-methylphenol.

(Step 2a)

Step 2a is a process for the preparation of a compound (IIa) which is a new intermediate of the present invention. Specifically, this step is a process for the preparation of a compound (IIa) by reacting N-(5-chloro-2-nitrophenyl)-N-methylamine with or without isolation from the reaction mixture obtained in Step 1 with a compound (V), one of the hydroxyaryl derivatives, in the presence of a base, and is described in particular as Step 2a. This step can be carried out in a similar manner to that described in Step 2.

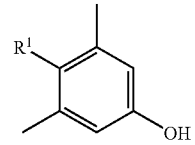

(V)

(wherein, $R^1$ has the same meaning as that indicated hereinbefore)

The base employed in this process can be used directly for the reaction as a salt prepared previously by reacting with the compound (V). The amount of the base employed in this process is, as described for Step 2, generally from 1 to 2 molar equivalents of the amount of compound (V) employed, preferably from 1 to 1.6 molar equivalents, and more preferably 1.2 molar equivalents.

The reaction temperature of this process is not particularly restricted, and is generally between 0° C. and refluxing temperature, preferably between room temperature and 180° C., and more preferably between 40° C. and 150° C.

The reaction time of this process is not particularly restricted, and is generally from 15 minutes to 24 hours, preferably from 15 minutes to 6 hours, and more preferably between 30 minutes and 3 hours.

After completion of the reaction of this process or a post-treatment of the reaction mixture, the product compound (IIa) is isolated from the reaction mixture acidified, neutralized or alkalized depending on the physico-chemical properties of the product by a conventional procedure, for example, extraction, collection by filtration, and the like. The isolated product can be used without any further treatment, or, if necessary, the isolated product is further purified before use by a conventional purification method such as distillation, re-crystallization, sublimation, partitioning, or chromatography.

In Step 2a, the yield and purity of the desired compound (IIa) may be lowered by oxidizable impurities formed as by-products as described for Step 2. In such cases, it is possible to suppress the formation of these impurities by degassing of the inert solvent employed, by addition of an antioxidant, or degassing of the inert solvent and addition of an antioxidant as described for Step 2, and consequently, the desired compound (IIa) can be obtained in high yield at high purity by a simple procedure. Such an antioxidant is not particularly restricted provided that its anti-oxidation effect is confirmed, and is preferably 2,4-di-t-butyl-4-methylphenol.

Procedures for the preparation of the compound (I) and its intermediate, the compound (III), of the present invention are described in detail hereinafter.

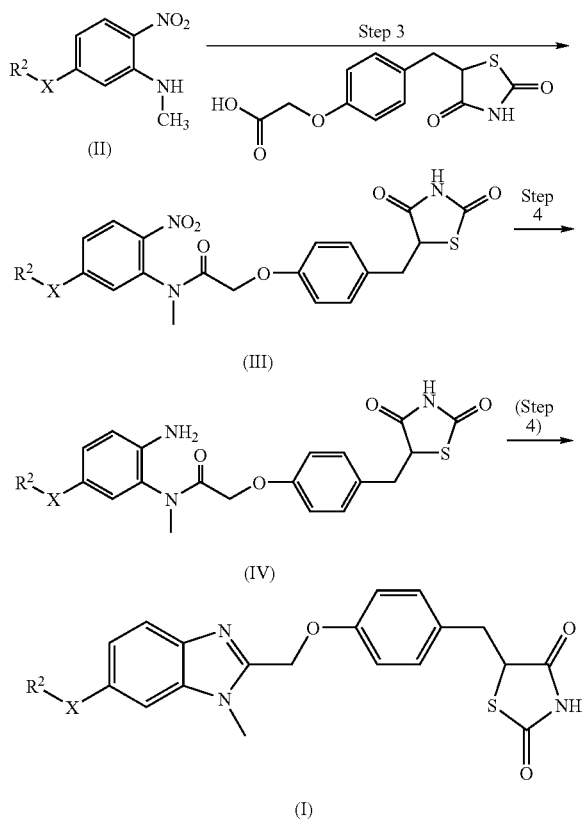

In the above reaction scheme and description hereinafter, $R^2$ and X have the same meanings as those indicated hereinbefore.

(Step 3)

Step 3 is a process for the preparation of a compound (III) of the present invention by condensing a compound (II) and 4-[(2,4-dioxothiazolidin-5-yl)methyl]phenoxyacetic acid.

This process is carried out by the acid halide method, the active ester method, or the mixed acid anhydride method, each of which is described in detail hereinafter.

(Acid Halide Method)

The acid halide method is carried out by the preparation of 4-[(2,4-dioxothiazolidin-5-yl)methyl]phenoxyacetyl halide by reacting 4-[(2,4-dioxothiazolidin-5-yl)methyl]phenoxyacetic acid with a halogenating agent such as thionyl chloride, oxalyl chloride, and the like in an inert solvent, followed by an amidation with the compound (II) or salt thereof in the presence or absence of a base in an inert solvent.

The halogenating agent used for halogenation reaction is not particularly restricted provided that it can convert a carboxylic acid to a corresponding acid halide. Such halogenating agent can be, for example, thionyl chloride, thionyl bromide, oxalyl chloride, phosphorus oxychloride, phosphorus trichloride, phosphorus pentachloride, and the like, and is preferably thionyl chloride, oxalyl chloride, or phosphorus pentachloride, and particularly preferably thionyl chloride.

The amount of the halogenating agent used for the halogenation reaction is not particularly restricted provided that it is more than 1 molar equivalent of the amount of 4-[(2,4-dioxothiazolidin-5-yl)methyl]phenoxyacetic acid employed, and is preferably from 1 to 2 molar equivalents, and more preferably from 1 to 1.2 molar equivalents.

The inert solvent employed is not particularly restricted provided that it has no adverse effect on the reaction. Such inert solvent is, for example, an aliphatic hydrocarbon such as hexane, heptane, ligroin, or petroleum ether; an aromatic hydrocarbon such as benzene, toluene or xylene; a nitrile such as acetonitrile, propionitrile, or benzonitrile; a halogenated hydrocarbon such as dichloromethane, chloroform, 1,2-dichloroethane, or carbon tetrachloride; an ether such as diethyl ether, diisopropyl ether, tetrahydrofuran, dioxane, dimethoxyethane, or diethylene glycol dimethyl ether; an amide such as formamide, dimethylformamide, dimethylacetamide, or hexamethylphosphoric triamide; a sulfoxide such as dimethyl sulfoxide; sulfolane; or a mixture thereof, preferably a halogenated aliphatic hydrocarbon, nitrile, ether or amide, or a mixture thereof, more preferably acetonitrile, dichloromethane, chloroform, tetrahydrofuran, dimethylformamide, or a mixture thereof, and particularly preferably dichloromethane or acetonitrile.

The halogenation reaction may proceed rapidly by addition of a catalyst in some instances.

The catalyst employed in the above reaction is generally an amine, an amine derivative or a heterocyclic compound having nitrogen atom(s).

When an amine is used, a tertiary amine can commonly be used, and such an amine is, for example, a trialkylamine such as trimethylamine, triethylamine, diisopropylethylamine, tributylamine, or the like; a dialkyarylamine such as N,N-dimethylaniline, N,N-diethylaniline, or the like; or a diaryalkylamine such as diphenylmethylamine, or the like.

The amine derivative employed in the above reaction is a N,N-dialkylamide such as dimethylformamide, dimethylacetamide, or the like.

The heterocyclic compound having nitrogen atom(s) is pyridine, N,N-dimethyl-4-aminopyridine, imidazole, triazole, or the like.

Preferably, the amine is trimethylamine, triethylamine, diisopropylethylamine, tributylamine, N,N-dimethylaniline, dimethylformamide, diethylacetamide, pyridine, or N,N-dimethyl-4-aminopyridine, more preferably the amine is triethylamine, dimethylformamide, pyridine, or N,N-dimethyl-4-aminopyridine, and particularly preferably the amine is dimethylformamide.

The amount of catalyst employed is not particularly restricted, and is generally from 0.01 to 20 molar equivalents of the amount of halogenating agent employed, preferably from 0.1 to 10 molar equivalents, and more preferably from 0.3 to 5 molar equivalents.

The reaction temperature of this process varies depending on the materials, the reagent(s) used, and the like, but is generally between −20° C. and 150° C., preferably between −10° C. and 100° C., and more preferably between −10° C. and 40° C.

The reaction time for the halogenation reaction varies depending on the materials, the reagent(s) used, the reaction temperature, and the like, but is generally from 30 minutes to 80 hours, preferably from 30 minutes to 48 hours, and more preferably from 1 to 6 hours.

After completion of the halogenation reaction, 4-[(2,4-dioxothiazolidin-5-yl)methyl]phenoxyacetyl halide or a salt thereof can be used for the amidation reaction with or without isolation from the reaction mixture, and preferably it is desirable to use said compound for the amidation reaction without isolation.

The amidation reaction is a process for the preparation of a compound (III), and is accomplished by reacting 4-[(2,4-dioxothiazolidin-5-yl)methyl]phenoxyacetyl halide with a compound (II) in an inert solvent.

In this process, the reaction may proceed rapidly by addition of a base in some instances. When a base is used in this process, the base employed can be, for example, an alkali metal carbonate such as lithium carbonate, sodium carbonate, or potassium carbonate; an alkali metal hydrogencarbonate such as lithium hydrogencarbonate, sodium hydrogencarbonate, or potassium hydrogencarbonate; an alkali metal hydride such as lithium hydride, sodium hydride or potassium hydride; an alkali metal hydroxide such as lithium hydroxide, sodium hydroxide, or potassium hydroxide; an alkali metal alkoxide such as lithium methoxide, sodium methoxide, sodium ethoxide, or potassium tert-butoxide; and an organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO), or 1,8-diazabicyclo[5.4.0]undec-7-ene (DBU), and is preferably an organic amine, more preferably triethylamine, tributylamine or pyridine, and particularly preferably triethylamine.

The amidation reaction is generally carried out in an inert solvent. The inert solvent employed for this reaction is not particularly restricted provided that it has no adverse effect on the reaction. Such an inert solvent can be, for example, an aliphatic hydrocarbon such as hexane, heptane, ligroin, or petroleum ether; an aromatic hydrocarbon such as benzene, toluene or xylene; a nitrile such as acetonitrile, propionitrile, or benzonitrile; a halogenated hydrocarbon such as dichloromethane, chloroform, 1,2-dichloroethane, or carbon tetrachloride; an ether such as diethyl ether, diisopropyl ether, tetrahydrofuran, dioxane, dimethoxyethane, or diethylene glycol dimethyl ether; an amide such as formamide, dimethylformamide, dimethylacetamide, or hexamethylphosphoric triamide; a sulfoxide such as dimethyl sulfoxide; a sulfone such as sulfolane; or a mixture thereof, and is preferably a halogenated hydrocarbon, a nitrile, an ether, or an amide, or a mixture thereof, more preferably acetonitrile, dichloromethane, chloroform, tetrahydrofuran, dimethylformamide, or a mixture thereof, and particularly preferably dichloromethane or acetonitrile.

The reaction temperature for the amidation reaction varies depending on the materials, the reagent(s) used, and the like, but is generally between −20° C. and 150° C., and preferably between −20° C. and 100° C.

The reaction time for the amidation reaction varies depending on the materials, the reagent(s) used, the reaction temperature, and the like, but is generally from 30 minutes to 80 hours, and preferably from 1 hour to 48 hours.

(Active Ester Method)

The active ester method is carried out by the preparation of an active ester by reacting 4-[(2,4-dioxothiazolidin-5-yl)methyl]phenoxyacetic acid with an active esterification agent, followed by the preparation of a compound (III) by reacting the resulting active ester with a compound (II) in the presence or absence of a base in an inert solvent.

The active esterification agent used in the active ester method can be, for example, a N-hydroxy compound such as N-hydroxysuccinimide, 1-hydroxybenztriazole, or N-hydroxy-5-norbornene-2,3-dicarboximide; a disulfide compound such as dipyridyl disulfide; a carbodiimide such as dicyclohexylcarbodiimide; or a condensation agent such as carbonyldiimidazole or triphenylphosphine.

The inert solvent employed for the active ester method is not particularly restricted provided that it has no adverse effect on the reaction. Such an inert solvent can be, for example, an aliphatic hydrocarbon such as hexane, heptane, ligroin, or petroleum ether; an aromatic hydrocarbon such as benzene, toluene or xylene; a nitrile such as acetonitrile, propionitrile, or benzonitrile; a halogenated hydrocarbon such as dichloromethane, chloroform, 1,2-dichloroethane, or carbon tetrachloride; an ether such as diethyl ether, diisopropyl ether, tetrahydrofuran, dioxane, dimethoxyethane, or diethylene glycol dimethyl ether; an amide such as formamide, dimethylformamide, dimethylacetamide, or hexamethylphosphoric triamide; a sulfoxide such as dimethyl sulfoxide; a sulfolane; or a mixture thereof, and is preferably a halogenated hydrocarbon, a nitrile, an ether or an amide, and a mixture thereof, more preferably acetonitrile, dichloromethane, chloroform, tetrahydrofuran, dioxane, dimethylformamide, or a mixture thereof, and particularly preferably tetrahydrofuran, dioxane, or acetonitrile.

When a base is used in the active ester method, the same base as that described in the acid halide method can be used.

The reaction temperature for the active ester method varies depending on the materials, the reagent(s) used, and the like, but is generally between −70° C. and 150° C., and preferably between −20° C. and 100° C.

The reaction time for the active ester method varies depending on the materials, the reagent(s) used, the reaction temperature, and the like, but is generally from 10 minutes to 80 hours, and preferably from 30 minutes to 12 hours.

(Mixed Acid Anhydride Method)

The mixed acid anhydride method is carried out by the preparation of a mixed acid anhydride by reacting 4-[(2,4-dioxothiazolidin-5-yl)methyl]phenoxyacetic acid with a reagent for the formation of a mixed acid anhydride, followed by the preparation of a compound (III) by reacting the resulting mixed acid anhydride with a compound (II) in the presence or absence of a base in an inert solvent.

The reagent for formation of the mixed acid anhydride employed in the mixed acid anhydride method can be, for example, an alkanoyl halide such as acetyl chloride or pivaloyl chloride; a chlorocarbonate such as methyl chlorocarbonate, ethyl chlorocarbonate, or phenyl chlorocarbonate; or a cyanophosphonate such as diethyl cyanophosphonate or diphenyl cyanophosphonate.

The inert solvent employed in the mixed acid anhydride method is not particularly restricted provided that it has no adverse effect on the reaction. Such inert solvent can be, for example, an aliphatic hydrocarbon such as hexane, heptane, ligroin, or petroleum ether; an aromatic hydrocarbon such as benzene, toluene, or xylene; a nitrile such as acetonitrile, propionitrile, or benzonitrile; a halogenated hydrocarbon such as dichloromethane, chloroform, 1,2-dichloroethane, or carbon tetrachloride; an ether such as diethyl ether, diisopropyl ether, tetrahydrofuran, dioxane, dimethoxyethane, or diethylene glycol dimethyl ether; an amide such as formamide, dimethylformamide, dimethylacetamide, or hexamethylphosphoric triamide; a sulfoxide such as dimethyl sulfoxide; a sulfolane; or a mixture thereof, and is preferably a halogenated hydrocarbon, a nitrile, an ether or an amide, or a mixture thereof, more preferably acetonitrile, dichloromethane, chloroform, tetrahydrofuran, dioxane, dimethylformamide, or a mixture thereof, and particularly preferably tetrahydrofuran, dioxane, or acetonitrile.

When a base is used in the mixed acid anhydride method, the same base as that described in the acid halide method can be used.

The reaction temperature for the mixed acid anhydride method varies depending on the materials, the reagent(s) used, and the like, but is generally between −70° C. and 150° C., and preferably between 20° C. and 100° C.

The reaction time for the mixed acid anhydride method varies depending on the materials, the reagent(s) used, the reaction temperature, and the like, but is generally from 10 minutes to 80 hours, and preferably from 30 minutes to 12 hours.

After the completion of each reaction of the acid halide method, the active ester method, and the mixed acid anhydride method, a compound (III) can be isolated by extraction or spontaneous crystallization from the reaction mixture after a conventional post-treatment or neutralization, if necessary. Compound (III) thus obtained can be used for the subsequent reaction without any further treatment, or, if necessary, the isolated product is purified before use by a conventional purification method such as recystallization, reprecipitation, or chromatography.

(Step 4)

Step 4 is a process for the preparation of a compound (I) or a pharmaceutically acceptable salt thereof by reduction of a nitro group of a compound (III), followed by intramolecular dehydration condensation, and proceeds through a compound (IV) as an intermediate.

The reduction of the nitro group in this process can be carried out by a known method that has been commonly used for reducing a nitro group, but is generally carried out by catalytic hydrogenation.

The catalyst employed in this process is not particularly restricted provided that it can be generally used for catalytic hydrogenation. Such a catalyst can be, for example, palladium-carbon, platinum-carbon, Raney nickel, Wilkinson's complex, or the like, and is preferably palladium-carbon or platinum-carbon.

The pressure of hydrogen in this process is not particularly restricted provided that it is higher than one atmospheric pressure. It is generally between from 1 to 20 atmospheric pressures, and preferably between from 1 to 10 atmospheric pressures.

The solvent employed in this process is not particularly restricted provided that it dissolves the compound (III) to at least some extent and that it has no adverse effect on the reaction. Such a solvent can be, for example, an aliphatic hydrocarbon such as hexane, heptane, ligroin, petroleum ether, cyclohexane or methylcyclohexane; an aromatic hydrocarbon such as benzene, toluene, or xylene; a carboxylic acid such as acetic acid; a carboxylic acid ester such as ethyl acetate or butyl acetate; a nitrile such as acetonitrile, propionitrile, or benzonitrile; an ether such as diethyl ether, diisopropyl ether, tetrahydrofuran, dioxane, dimethoxyethane, or diethylene glycol dimethyl ether; an amide such as formamide, dimethylformamide, dimethylacetamide, or hexamethylphosphoric triamide; or a mixture thereof, and is preferably an alcohol, a carboxylic acid, a carboxylic acid ester, a nitrile, an ether or an amide, or a mixture thereof, more preferably methanol, a carboxylic acid ester, acetonitrile, tetrahydrofuran, dimethylacetamide, or a mixture thereof, and particularly preferably methanol, or a mixed solvent of methanol and dimethylacetamide.

In this process, the reaction may proceed rapidly by addition of an acid. Additionally, in some cases, an appropriate acid is added to prepare a pharmaceutically acceptable salt of compound (I) directly.

The acid employed in this process is not particularly restricted, and can be, for example, an organic acid such as hydroxyacetic acid, oxalic acid, or citric acid; or a halogenated hydroacid such as hydrochloric acid, or bromic acid, and is preferably hydrochloric acid.

When the acid is added in this process, the amount of acid added is not particularly restricted, and is generally from 1 to 100 molar equivalents of the amount of compound (IV) employed, and preferably from 1 to 10 molar equivalents.

The reaction temperature of this process is not particularly restricted, and is generally between 0° C. and 150° C., and preferably between room temperature and 100° C.

After completion of the reaction of this process, the reaction mixture is acidified, neutralized or alkalized depending on the physico-chemical properties of the product after a conventional post-treatment, and the product compound is isolated. The isolated product may be obtained as a pure compound, and, if necessary, the isolated product is further purified by a conventional purification method such as re-crystallization or chromatography.

EXAMPLES

The present invention is described in more detail hereinafter by way of the Examples, but the scope of the present invention should not be limited to these examples.

Example 1

N-[5-(4-Amino-3,5-dimethylphenoxy)-2-nitrophenyl]-N-methylamine (Step 2a)

To a solution of N-(5-chloro-2-nitrophenyl)-N-methylamine (4.0 g) in N,N-dimethylacetamide (56 ml) were added 4-amino-3,5-dimethylphenol (2.9 g) and potassium t-butoxide (2.9 g) with stirring under ice-cooling, and the resulting mixture was stirred at 75-80° C. for 1 hour. After stirring, water (74 ml) was added to the reaction mixture, and the resulting mixture was cooled gradually to room temperature. The crystals precipitated were collected by filtration and dried in vacuo to afford the title compound (4.9 g, yield: 80%) as a yellow crystalline solid.

NMR (400 MHz, CDCl$_3$) δ ppm: 2.20 (s, 6H), 2.90 (d, J=4.9 Hz, 3H), 3.57 (s, 2H), 6.16-6.21 (m, 2H), 6.71 (s, 2H), 8.11 (d, J=9.3 Hz, 1H), 8.20 (brs, 1H).

Example 2

N-[5-(4-Amino-3,5-dimethylphenoxy)-2-nitrophenyl]-N-methylamine (Step 2a)

To a solution of N-(5-chloro-2-nitrophenyl)-N-methylamine (8.00 g) in N,N-dimethylacetamide (112 ml) was added 2,6-di-t-butyl-4-methylphenol (0.24 g). Furthermore, to the resulting mixture were added 4-amino-3,5-dimethylphenol (6.47 g) and potassium t-butoxide (5.29 g) with stirring, and the resulting mixture was stirred at 60° C. for 30 minutes. After stirring, water (4 ml) was added to the reaction mixture, and furthermore water (120 ml) was added dropwise over a 2-hour interval, and then the resulting mixture was cooled gradually to room temperature. The crystalline solid precipitated was collected by filtration, washed with water (80 ml) and dried in vacuo to afford the title compound (11.45 g, yield: 93%) as a yellow crystalline solid.

The title compound thus obtained showed the same nuclear magnetic resonance spectrum as that of the product obtained in Example 1.

Example 3

N-[5-(3,5-Dimethyl-4-nitrophenoxy)-2-nitrophenyl]-N-methylamine (Step 2a)

To a solution of N-(5-chloro-2-nitrophenyl)-N-methylamine (0.86 g) and 3,5-dimethyl-4-nitrophenol (0.76 g) in N,N-dimethylacetamide (12 ml) was added potassium t-butoxide (0.554 g) at room temperature, and the resulting mixture was stirred successively at the same temperature for 20 minutes, at 100° C. for 10 minutes, at 125° C. for 45 minutes, and at 140° C. for 1 hour. After cooling the reaction mixture to 0° C., the reaction mixture was adjusted to a pH of about 3 with 3N hydrochloric acid. The crystalline solid precipitated was collected by filtration, washed successively with 3N hydrochloric acid and water and air-dried for 3 days to afford the title compound (1.16 g, yield: 80%).

NMR (400 MHz, CDCl$_3$) δ ppm: 2.32 (s, 6H), 2.97 (d, J=5.1 Hz, 3H), 6.23 (dd, J=9.5 Hz, J=2.4 Hz, 1H), 6.36 (d, J=2.4 Hz, 1H), 6.82 (s, 2H), 8.20 (d, J=9.5 Hz, 1H).

Example 4

N-(5-Methoxy-2-nitrophenyl)-N-methylamine (Step 1 and Step 2)

To a solution of 2,4-dichloronitrobenzene (3.0 g) in N,N-dimethylacetamide (30 ml) was added a 40% aqueous solution of methylamine (4.9 g) at room temperature, and the resulting mixture was stirred at 75-80° C. for 2 hours. Subsequently, to the reaction mixture was added a 28% methanolic solution of sodium methoxide (7.6 g), and the resulting mixture was stirred at the same temperature for 1.5 hours. Furthermore, to the reaction mixture was added a 28% methanolic solution of sodium methoxide (1.6 g), and the resulting mixture was stirred at the same temperature for 1 hour. After stirring, water (60 ml) was added to the reaction mixture, and the resulting mixture was cooled gradually to room temperature. The crystalline solid precipitated was collected by filtration and dried in vacuo to afford the title compound (2.2 g, yield: 77%) as a yellow crystalline solid.

NMR (400 MHz, CDCl$_3$) δ ppm: 3.01 (d, J=4.9 Hz, 3H), 3.89 (s, 3H), 6.13 (d, J=2.4 Hz, 1H), 6.25 (dd, J=9.5 Hz, J=2.7 Hz, 1H), 8.16 (d, J=9.5 Hz, 1H), 8.29 (brs, 1H).

Example 5

N-[5-(4-Amino-3,5-dimethylphenoxy)-2-nitrophenyl]-N-methylamine (Step 1 and Step 2)

To a solution of 2,4-dichloronitrobenzene (3.0 g) in N,N-dimethylacetamide (30 ml) was added a 40% aqueous solution of methylamine (4.9 g) at room temperature, and the resulting mixture was stirred at 75-80° C. for 1.5 hours. To the reaction mixture were added 4-amino-3,5-dimethylphenol (2.2 g), potassium t-butoxide (3.5 g), and N,N-dimethylacetamide (15 ml), and the resulting mixture was stirred at the same temperature for 3 hours. After stirring, water (60 ml) was added to the reaction mixture, and the resulting mixture was cooled gradually to room temperature. The crystalline solid precipitated was collected by filtration and dried in vacuo to afford the title compound (3.0 g, yield: 67%) as a yellow crystalline solid.

The nuclear magnetic resonance spectrum of the title compound thus obtained agreed with that of the product obtained in Example 1.

Example 6

N-[5-(4-t-Butoxycarbonylamino-3,5-dimethylphenoxy)-2-nitrophenyl]-N-methylamine

To a solution of N-[5-(4-amino-3,5-dimethylphenoxy)-2-nitrophenyl]-N-methylamine (40.00 g) obtained in Example 5 in toluene (400 ml) were added triethylamine (21.13 g) and di-t-butyl dicarbonate (33.42 g) at room temperature, and the resulting mixture was refluxed for 3 hours. Furthermore, to the reaction mixture were added di-t-butyl dicarbonate (12.15 g) and triethylamine (7.04 g), and the resulting mixture was further refluxed for 2 hours. After cooling to room temperature, the reaction mixture was washed successively with 10% hydrochloric acid for 3 times (100 ml each), 20% hydrochloric acid twice (60 ml each), a 5% aqueous solution of sodium hydrogencarbonate twice (100 ml each) and water (100 ml). The organic layer separated was kept in a refrigerator overnight, and to the reaction mixture was added ethylcyclohexane (120 ml), and the resulting mixture was stirred at 0° C. for 1 hour. The crystalline solid precipitated was collected by filtration, washed with a mixed solvent of toluene and ethylcyclohexane (1:4, 100 ml) cooled previously to 0° C. and dried at 40° C. in vacuo to afford the title compound (48.79 g, yield: 91%).

NMR (400 MHz, CDCl$_3$) δ ppm: 1.53 (brs, 9H), 2.27 (s, 6H), 2.93 (d, J=4.9 Hz, 3H), 5.84 (brs, 1H), 6.20 (dd, J=2.4 Hz, J=9.5 Hz, 1H), 6.31 (brs, 1H), 6.80 (s, 2H), 8.14 (d, J=9.5 Hz, 1H), 8.19 (brd, 1H).

Example 7

N-[5-(3,5-Dimethyl-4-nitrophenoxy)-2-nitrophenyl]-2-{4-[2,4-dioxo-1,3-thiazolidin-5-yl] methyl}phenoxy}-N-methylacetamide (Step 3) (Exemplification compound number: 211)

To a suspended solution of 4-[(2,4-dioxothiazolidin-5-yl)methyl]phenoxyacetic acid (1.07 g) in acetonitrile (10 ml) were added thionyl chloride (0.46 g) and dimethylformamide (0.2 ml) at 0° C., and the resulting mixture was stirred successively at the same temperature for 20 minutes, at 10° C. for 20 minutes, at 30° C. for 20 minutes, and at 40° C. for 30 minutes. Subsequently, to the reaction mixture were added N-[5-(3,5-dimethyl-4-nitrophenoxy)-2-nitrophenyl]-N-methylamine (1.01 g) and N,N-dimethylaminopyridine (0.04 g), and the resulting mixture was stirred at 53° C. for 2 hours. After cooling the reaction mixture to 0° C., 3N hydrochloric acid (30 ml) was added to the reaction mixture, and the resulting mixture was extracted with ethyl acetate (80 ml). The organic layer was washed with a saturated aqueous solution of sodium hydrogencarbonate (16 ml), dried over anhydrous magnesium sulfate and evaporated to dryness to afford the title compound (2.09 g, yield: 99%) as an orange-colored amorphous solid.

The nuclear magnetic resonance spectrum (as the title compound obtained is a mixture of two atropisomers, only the characteristic and assignable peaks, which can be distinguished on the spectrum, are given.) (400 MHz, CDCl$_3$) δ ppm: 2.33 (s, 6H, Ar—CH$_3$), 3.26 and 3.27 (s, 3H, NCH$_3$), 8.09 (brm, 1H, CONHCO).

Example 8

2-{4-[(2,4-Dioxo-1,3-thiazolidin-5-y)methyl]phenoxy}-N-(5-methoxy-2-nitrophenyl)-N-methylacetamide (Step 3) (Exemplification compound number: 1)

To a suspended solution of 4-[(2,4-dioxothiazolidin-5-yl)methyl]phenoxyacetic acid (8.00 g) in acetonitrile (64 ml) were added thionyl chloride (3.38 g) and dimethylformamide (3.2 ml) at room temperature, and the resulting mixture was stirred successively at 25° C. for 30 minutes and at 40° C. for 30 minutes. Subsequently, to the reaction mixture were added successively N-(5-methoxy-2-nitrophenyl)-N-methylamine (3.84 g), N,N-dimethylaminopyridine (0.32 g) and acetonitrile (16 ml), and the resulting mixture was stirred at the same temperature for 1 hour. After cooling the reaction mixture to 0° C., water (32 ml) was added to the reaction mixture, and the resulting mixture was extracted with ethyl acetate (80 ml). The organic layer was washed with a saturated aqueous solution of sodium hydrogencarbonate twice (16 ml for each) and evaporated to dryness to afford the title compound (9.67 g, yield: 100%) as an orange-colored amorphous solid.

The nuclear magnetic resonance spectrum (as the title compound obtained is a mixture of two atropisomers, only the assignable peaks of the isomer with high content ratio are given.) (400 MHz, DMSO-d$_6$) δ ppm: 2.9-3.1 (m, 2H), 3.2 (s, 3H), 3.91 (s, 3H), 4.36 (d, J=14.9 Hz, 1H), 4.54 (d, J=14.9 Hz, 1H), 4.6-4.9 (m, 1H), 4.99 (brs, 1H), 6.76 (d, J=8.8 Hz, 2H), 7.0-7.2 (m, 4H), 7.35 (d, J=2.4 Hz, 1H), 8.21 (d, J=9.3 Hz, 1H).

Example 9

4-{3-[({4-[(2,4-Dioxo-1,3-thiazolidin-5-yl)methoxy]phenoxy}acetyl)(methyl)amino]-4-nitrophenoxy}-2,6-dimethylphenylcarbamic acid t-butyl ester (Step 3) (Exemplification compound number: 210)

To a suspension of 4-[(2,4-dioxothiazolidin-5-yl)methyl]phenoxyacetic acid (15.00 g) in acetonitrile (150 ml) were added thionyl chloride (6.92 g) and dimethylformamide (12.0 ml) at room temperature, and the resulting mixture was stirred at room temperature for 1.5 hours. Subsequently, to the reaction mixture were added successively a solution of N-[5-(4-t-butoxycarbonylamino-3,5-dimethylphenoxy)-2-nitrophenyl]-N-methylamine (20.00 g) in a mixed solvent of dimethylformamide (60 ml) and acetonitrile (75 ml), and acetonitrile (35 ml) with stirring. Furthermore, to the resulting mixture was added N,N-dimethylaminopyridine (2.61 g), and the resulting mixture was stirred for 5 hours. After stirring, ethyl acetate (300 ml) was added to the reaction mixture, and the organic layer was washed successively with a 20% aqueous solution of sodium chloride (100 ml), a 5% aqueous solution of sodium hydrogencarbonate (100 ml) and water (100 ml), dried over anhydrous magnesium sulfate and evaporated. The residue obtained was purified by chromatography on a silica gel column using a mixed solvent of ethyl acetate and hexane (1:10-2:1) as the eluent to afford the title compound (24.44 g, yield: 70%) as a yellow crystalline solid.

The nuclear magnetic resonance spectrum (as the title compound thus obtained is a mixture of two atropisomers, only the characteristic and assignable peaks, which can be distinguished on the spectrum, are given.) (400 MHz, CDCl$_3$) δ ppm: 1.52 (brs, 9H, C(CH$_3$)$_3$), 2.271 and 2.275 (s, 6H, Ar—CH$_3$), 3.25 (s, 3H, NCH$_3$), 5.97 (brm, 1H, CONH—Ar), 9.00 (brm, 1H, CONHCO).

Example 10

5-[4-(6-Methoxy-1-methyl-1-H-benzimidazol-2-ylmethoxy)benzyl]thiazolidin-2,4-dione hydrochloride (Step 4)

To a solution of 2-{4-[(2,4-dioxo-1,3-thiazolidin-5-yl)methyl]phenoxy}-N-(5-methoxy-2-nitrophenyl)-N-methylacetamide (444.7 mg) in a mixed solvent of methanol (20 ml) and dimethylacetamide (5 ml) were added successively concentrated hydrochloric acid (0.344 ml) and a 10% wet palladium-carbon catalyst (244 mg). The atmosphere in the reaction flask was replaced with hydrogen gas (5 kg/cm$^2$), and the resulting mixture was shaken at 50° C. for 3.5 hours. After shaking, the reaction mixture was cooled to room temperature and filtered to obtain a pale yellow filtrate. When the filtrate obtained was concentrated to about 5 g, the product crystallized out of solution. The crystals precipitated were collected by filtration and washed with methanol to afford the title compound (210 mg, yield: 48%) as a white crystalline solid.

NMR (500 MHz, DMSO-d$_6$) δ ppm: 3.11 (dd, J=8.9 Hz, J=14.2 Hz, 1H), 3.34 (dd, J=4.5 Hz, J=14.2 Hz, 1H), 3.88 (s, 3H), 3.96 (s, 3H), 4.90 (dd, J=4.5 Hz, J=8.9 Hz, 1H), 5.60 (s, 2H), 7.12 (brm, J=8.7 Hz, 1H), 7.12 (d, J=8.7 Hz, 2H), 7.25 (d, J=8.7 Hz, 2H), 7.46 (d, J=2.0 Hz, 1H), 7.70 (d, J=8.7 Hz, 1H), 12.03 (s, 1H).

Example 11

5-(4-{[6-(4-Amino-3,5-dimethylphenoxy)-1-methyl-1-H-benzimidazol-2-yl]methoxy}benzyl)-1,3-thiazolidin-2,4-dione dihydrochloride (Step 4)

To a solution of 4-{3-[({4-[(2,4-dioxo-1,3-thiazolidin-5-yl)methoxy]phenoxy}acetyl)(methyl)amino]-4-nitrophenoxy}-2,6-dimethylphenylcarbamic acid t-butyl ester (1.00 g) in methanol (10 ml) were added successively 7.5% palladium-carbon (100 mg) and 38% hydrochloric acid (0.74 g), and after the atmosphere in the reaction flask was replaced with nitrogen gas followed by replacement of the nitrogen gas with hydrogen gas (4 kg/cm$^2$), the resulting mixture was shaken at 52° C. for 5 hours. After cooling the reaction mixture to room temperature, insoluble substance was filtered off to obtain the filtrate. The insoluble substance separated was washed with methanol (30 ml), and the washings and the filtrate obtained above were combined and evaporated to dryness. The residue obtained was dissolved in methanol (18 ml), and to the solution were added successively 38% hydrochloric acid (0.62 g) and methanol (2 ml), and the resulting mixture was refluxed for 4 hours. After cooling the reaction mixture to room temperature, the crystals precipitated were collected by filtration and washed with methanol (5 ml) to afford the title compound (230 mg, yield: 26%) as a pale yellow crystalline solid.

NMR (400 MHz, CD$_3$OD) δ ppm: 2.40 (s, 6H), 3.19 (dd, J=8.5 Hz, J=13.9 Hz, 1H), 3.39 (dd, J=3.9 Hz, J=13.9 Hz, 1H), 4.03 (s, 3H), 4.74 (dd, J=3.9 Hz, J=8.5 Hz, 1H), 5.71 (s, 2H), 6.91 (s, 2H), 7.15 (d, J=8.8 Hz, 2H), 7.30 (dd, J=8.8 Hz, 2H), 7.34 (dd, J=2.2 Hz, 1H), 7.61 (d, J=2.2 Hz, 1H), 7.83 (d, J=8.8 Hz, 1H).

The invention claimed is:

1. A compound having the formula (IIa) shown below

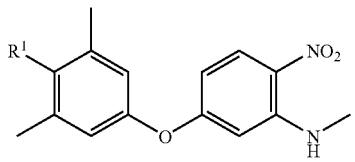

(IIa)

wherein
R¹ represents a nitro group, an amino group, or a t-butoxycarbonylamino group.

2. A method for the preparation of a compound having the following formula (II) comprising preparing N-(5-chloro-2-nitrophenyl)-N-methylamine by reacting 2,4-dichloronitrobenzene with methylamine, followed by reacting the resulting N-(5-chloro-2-nitrophenyl)-N-methylamine without isolation with a compound having a formula of R²—X—H in the presence of a base,
wherein
R² represents a hydrogen atom,
a $C_1$-$C_6$ alkyl group which is unsubstituted or substituted with from 1 to 5 substituents from a Substituent group α,
a $C_3$-$C_6$ cycloalkyl group which is unsubstituted or substituted with from 1 to 5 substituents selected from the group consisting of the Substituent group α, a $C_1$-$C_6$ alkyl group and a halomethyl group,
a phenyl group which is unsubstituted or substituted with from 1 to 5 substituents selected from the group consisting of the Substituent group α, a $C_1$-$C_6$ alkyl group and a halomethyl group, or
a 5- or 6-membered heterocyclic group which is unsubstituted or substituted with from 1 to 5 substituents selected from the group consisting of the Substituent group α, a $C_1$-$C_6$ alkyl group and a halomethyl group, said heterocyclic group contains from 1 to 4 heteroatoms selected from the group consisting of a nitrogen atom, an oxygen atom and a sulfur atom, and
X represents an oxygen atom, a sulfur atom or a nitrogen atom, said nitrogen atom is unsubstituted or substituted with one or more substituents selected from the group consisting of a hydrogen atom, a $C_1$-$C_6$ alkyl group, a $C_1$-$C_6$ alkylcarbonyl group, a $C_6$-$C_{10}$ arylcarbonyl group, a $C_1$-$C_6$ alkylsulfonyl group and a $C_6$-$C_{10}$ arylsulfonyl group,
the Substituent group α represents
a $C_3$-$C_6$ cycloalkyl group, a $C_2$-$C_6$ alkenyl group, a $C_2$-$C_6$ alkynyl group, a $C_6$-$C_{10}$ aryl group, a carboxyl group, a formyl group, a $C_1$-$C_6$ alkylcarbonyl group, a $C_6$-$C_{10}$ arylcarbonyl group, a $C_1$-$C_6$ alkyloxycarbonyl group, a $C_6$-$C_{10}$ aryloxycarbonyl group, a carbamoyl group, an N—$C_1$-$C_6$ alkylcarbamoyl group, an N,N-di($C_1$-$C_6$ alkyl)carbamoyl group, a hydroxyl group, a $C_1$-$C_6$ alkoxy group, a $C_6$-$C_{10}$ aryloxy group, a $C_1$-$C_6$ alkylcarbonyloxy group, a $C_6$-$C_{10}$ arylcarbonyloxy group, an amino group, a $C_1$-$C_6$ alkylamino group, a di($C_1$-$C_6$alkyl)amino group, a $C_6$-$C_{10}$ arylamino group, a di($C_6$-$C_{10}$ aryl)amino group, a mercapto group, a $C_1$-$C_6$ alkylthio group, a $C_6$-$C_{10}$ arylthio group, a $C_1$-$C_6$ alkylsulfinyl group, a $C_6$-$C_{10}$ arylsulfinyl group, a $C_1$-$C_6$ alkylsulfonyl group, a $C_6$-$C_{10}$ arylsulfonyl group, a sulfonic acid group, a halogen atom, a nitro group, and a cyano group,

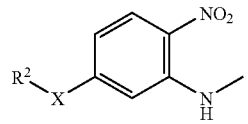

(II)

wherein R² and X represent the same meanings as those described above,
provided that the compound of formula (II) is not

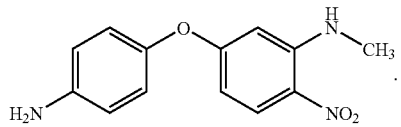

3. The method for the preparation of a compound according to claim 2, wherein R² represents a $C_1$-$C_6$ alkyl group or a phenyl group which is unsubstituted or substituted with from 1 to 3 substituents selected from the group consisting of a $C_1$-$C_6$ alkyl group, a halomethyl group, an amino group, a $C_1$-$C_6$ alkylamino group and a halogen atom; and X represents an oxygen atom.

4. A method for the preparation of a compound having the formula (IIa) indicated in claim 1 comprising reacting N-(5-chloro-2-nitrophenyl)-N-methylamine with a compound having the following formula (V) in the presence of a base in an inert solvent

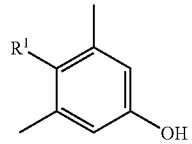

(V)

wherein
R¹ represents a nitro group, an amino group, or a t-butoxycarbonylamino group.

5. The method for the preparation of a compound according to claim 4, wherein the inert solvent is degassed.

6. The method for the preparation of a compound according to claim 4 which further comprises adding an antioxidant.

7. The method for the preparation of a compound according to claim 6, wherein the antioxidant employed is 2,6-di-t-butyl-4-methylphenol.

8. The method according to claim 5, which further comprises adding an antioxidant.

9. The method according to claim 8, wherein the antioxidant is 2,6-di-t-butyl-4-methylphenol.

10. The compound according to claim 1, wherein the compound is N-[5-(3,5-dimethyl-4-nitrophenoxy)-2-nitrophenyl]-N-methylamine.

11. The compound according to claim 1, wherein the compound is N-[5-(4-amino-3,5-dimethylphenoxy)-2-nitrophenyl]-N-methylamine.

12. The compound according to claim 1, wherein the compound is N-[5-(4-t-butoxycarbonylamino-3,5-dimethylphenoxy)-2-nitrophenyl]-N-methylamine.

* * * * *